United States Patent
Yang et al.

(10) Patent No.: US 10,100,026 B2
(45) Date of Patent: Oct. 16, 2018

(54) PROCESS FOR TREATING HOMOSERINE-BASED COMPOUND

(71) Applicants: CJ CHEILJEDANG CORPORATION, Seoul (KR); KOREA RESEARCH INSTITUTE OF CHEMICAL TECHNOLOGY, Daejeon (KR)

(72) Inventors: Young Lyeol Yang, Seoul (KR); Byung Sik Kim, Gyeonggi-do (KR); Jeong Hyun Kim, Jeollanam-do (KR); Jung Ho Lee, Daejeon (KR); Hyun Kwan Shin, Daejeon (KR); Ju Nam Kim, Daejeon (KR); Kyung Ho Cho, Gyeonggi-do (KR)

(73) Assignees: CJ Cheiljedang Corporation, Seoul (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/303,510

(22) PCT Filed: Apr. 10, 2015

(86) PCT No.: PCT/KR2015/003635
§ 371 (c)(1),
(2) Date: Oct. 11, 2016

(87) PCT Pub. No.: WO2015/156645
PCT Pub. Date: Oct. 15, 2015

(65) Prior Publication Data
US 2017/0037019 A1    Feb. 9, 2017

(30) Foreign Application Priority Data
Apr. 11, 2014 (KR) ......... 10-2014-0043860

(51) Int. Cl.
| | | |
|---|---|---|
| *C07D 307/32* | (2006.01) | |
| *C07D 307/33* | (2006.01) | |
| *C07D 307/46* | (2006.01) | |
| *C07D 307/58* | (2006.01) | |
| *C07C 29/149* | (2006.01) | |
| *C07C 51/363* | (2006.01) | |
| *C07C 51/367* | (2006.01) | |
| *C07C 67/317* | (2006.01) | |

(52) U.S. Cl.
CPC .......... *C07D 307/58* (2013.01); *C07C 29/149* (2013.01); *C07C 51/363* (2013.01); *C07C 51/367* (2013.01); *C07C 67/317* (2013.01); *C07D 307/32* (2013.01); *C07D 307/33* (2013.01); *C07D 307/46* (2013.01); *Y02P 20/582* (2015.11)

(58) Field of Classification Search
CPC .. C07D 307/32; C07D 307/33; C07D 307/46; C07D 307/58; C07C 29/149; C07C 51/363; C07C 51/367; C07C 67/317
See application file for complete search history.

(56) References Cited

U.S. PATENT DOCUMENTS

2008/0146840 A1    6/2008  Hateley et al.

OTHER PUBLICATIONS

Delhomme et al., "Succinic acid from renewable resources as a C4 building-block chemical—a review of the catalytic possibilities in aqueous media," Green Chem. 11:13-26, 2009.
Deng, "Nitrite anions induce nitrosative deamination of peptides and proteins," Rapid Commun. Mass Spectrom. 20: 3634-3638, 2006.
Itoh et al., "Reaction of Nitric Oxide with Amines," J. Org. Chem. 62: 3582-3585, 1997.
Labet et al., "Mechanism of nitric oxide induced deamination of cytosine," Phys. Chem. Chem. Phys., 11: 2379-2386, 2009.
Malin et al., "Deamination of Lysine as a Marker for Nitrite-Protein Reactions," J. Agric. Food Chem., vol. 37, No. 4, pp. 1071-1076, 1989.
Vasiliu et al., "Prediction of the Thermodynamic Properties of Key Products and Intermediates from Biomass. II," J. Phys. Chem. 116: 20738-20754, 2012.
Barrero et al., "Raney Nickel: An Effective Reagent for Reductive Dehalogenation of Organic Halides," Synlett 2001(4):485-488 (2001).
Gotoh et al. Improved synthesis and the crystal structure of methyl 4,6-dideoxy-4-(3-deoxy-L-glycero-tetronamido)-α-D-mannopyranoside, the methyl α-glycoside of the intracatenary repeating unit of the O-polysaccharide of Vibriocholerae O: 1Carbohydrate Research 260(2): 203-218 (1994).
Kenne et al., "Synthesis and Nuclear Magnetic Resonance Studies of Some N-Acylated Methyl 4-Amino-4,6-dideoxy-α-D-mannopyranosides," J. Chem. Soc. Perkin Trans. 1 5:1183-1186 (1988).
Lundin et al., "Asymmetric Suzuki Cross-Couplings of Activated Secondary Alkyl Electrophiles: Arylations of α-Chloroamides," Dept of Chemistry, MIT S1-S26 pages (2010).
Tanasova, et al., "An Unusual Conformation of α-Haloamides Due to Cooperative Binding with Zincated Porphyrins," Eur. J. Org. Chem S1-S106 (2009).

*Primary Examiner* — Timothy R Rozof
(74) *Attorney, Agent, or Firm* — Cooley LLP

(57) ABSTRACT

The present disclosure relates to the preparation of a useful compound, which can be used as an intermediate for preparing an important compound in the industrial field from a homoserine-based compound, and provides a process for treating a homoserine-based compound, capable of mass-producing a useful compound from a homoserine-based compound in a simple manner with excellent efficiency.

29 Claims, 16 Drawing Sheets

[FIG. 1]
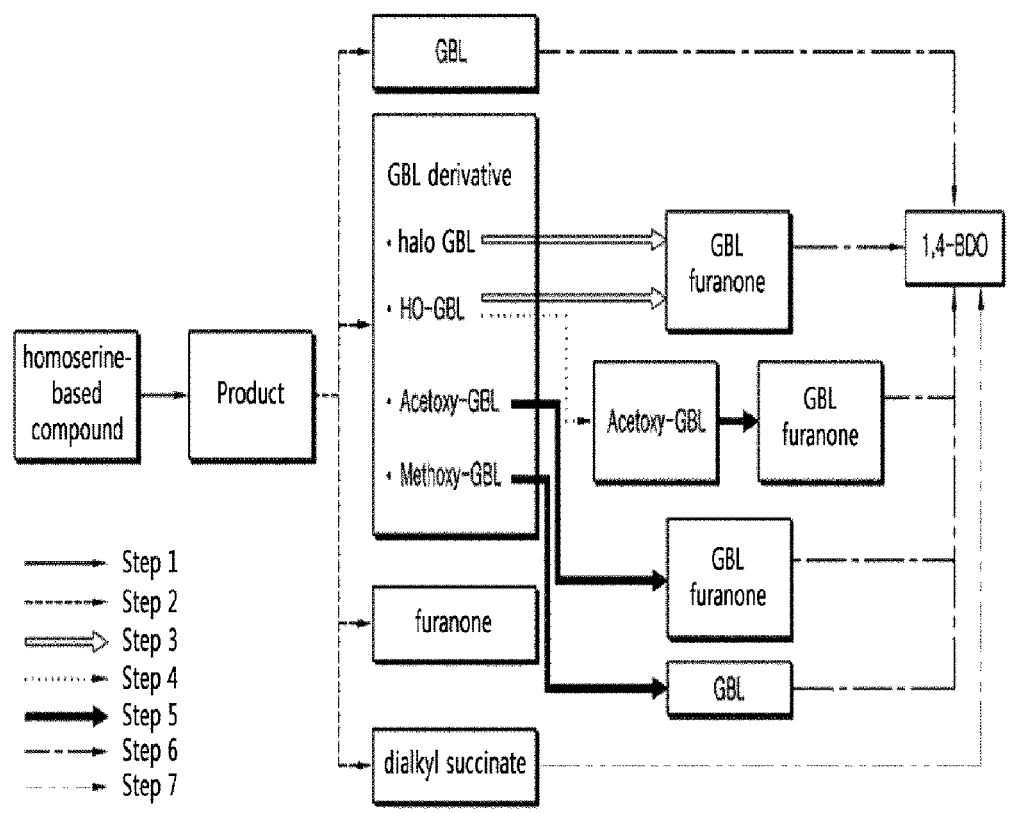

[FIG. 2]
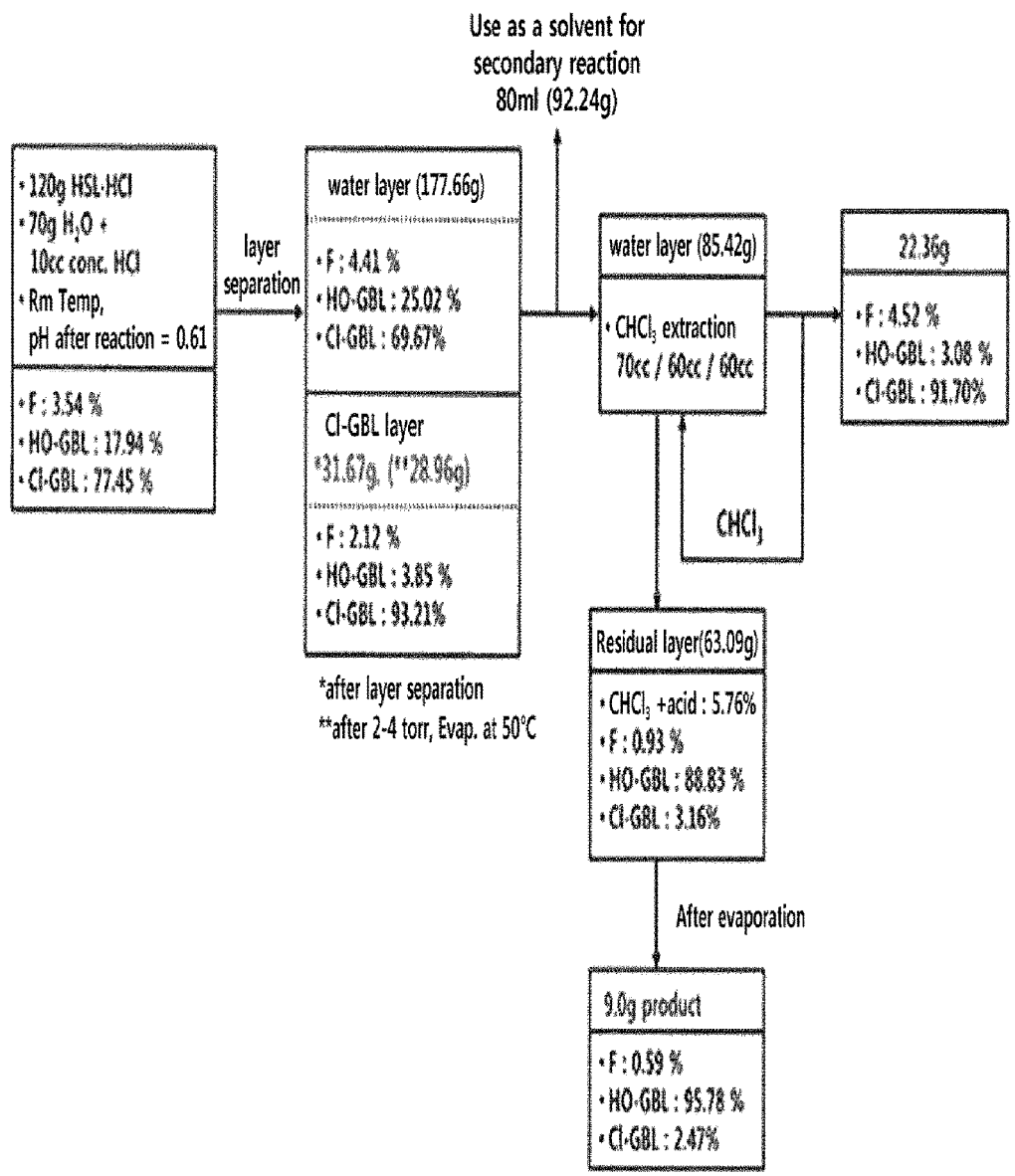

[FIG. 3]
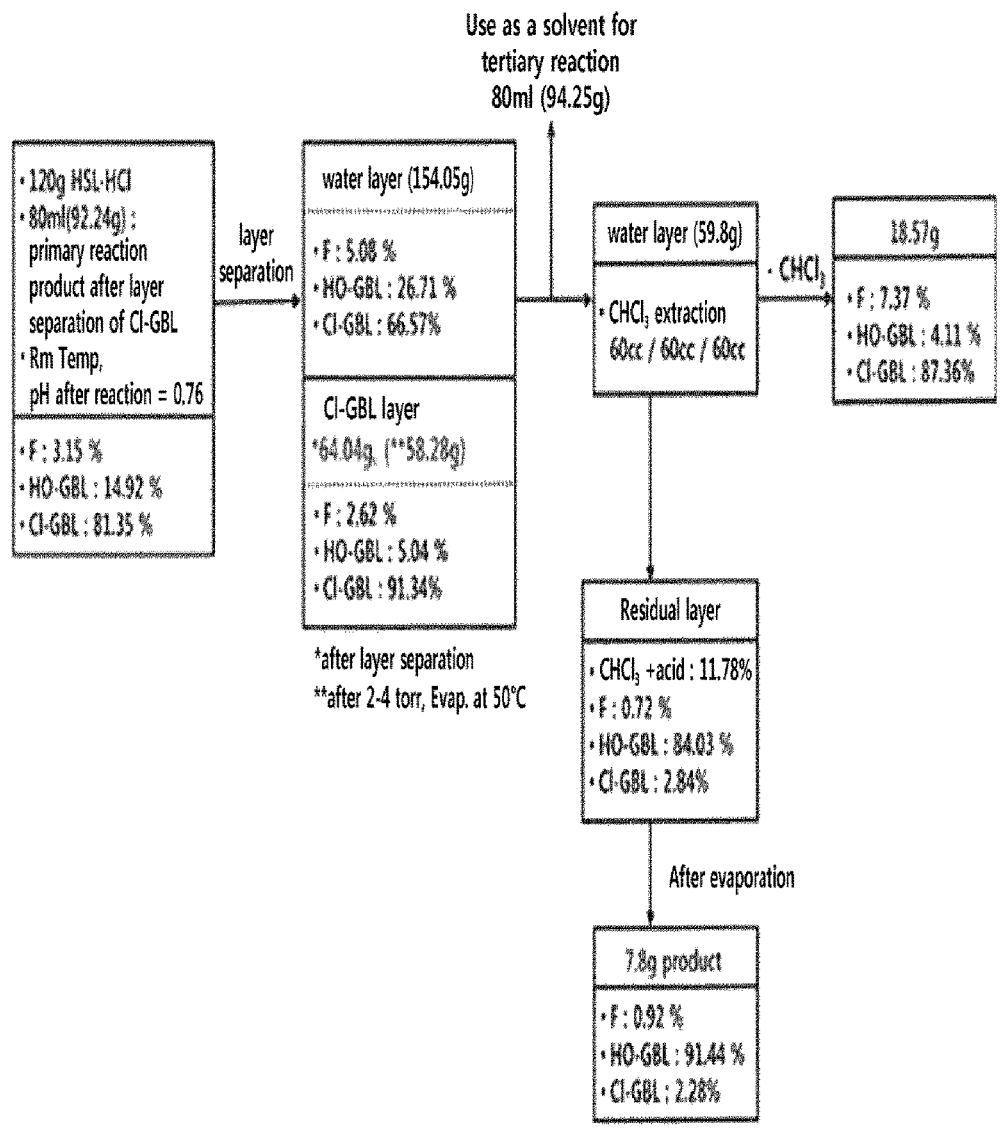

[FIG. 4]
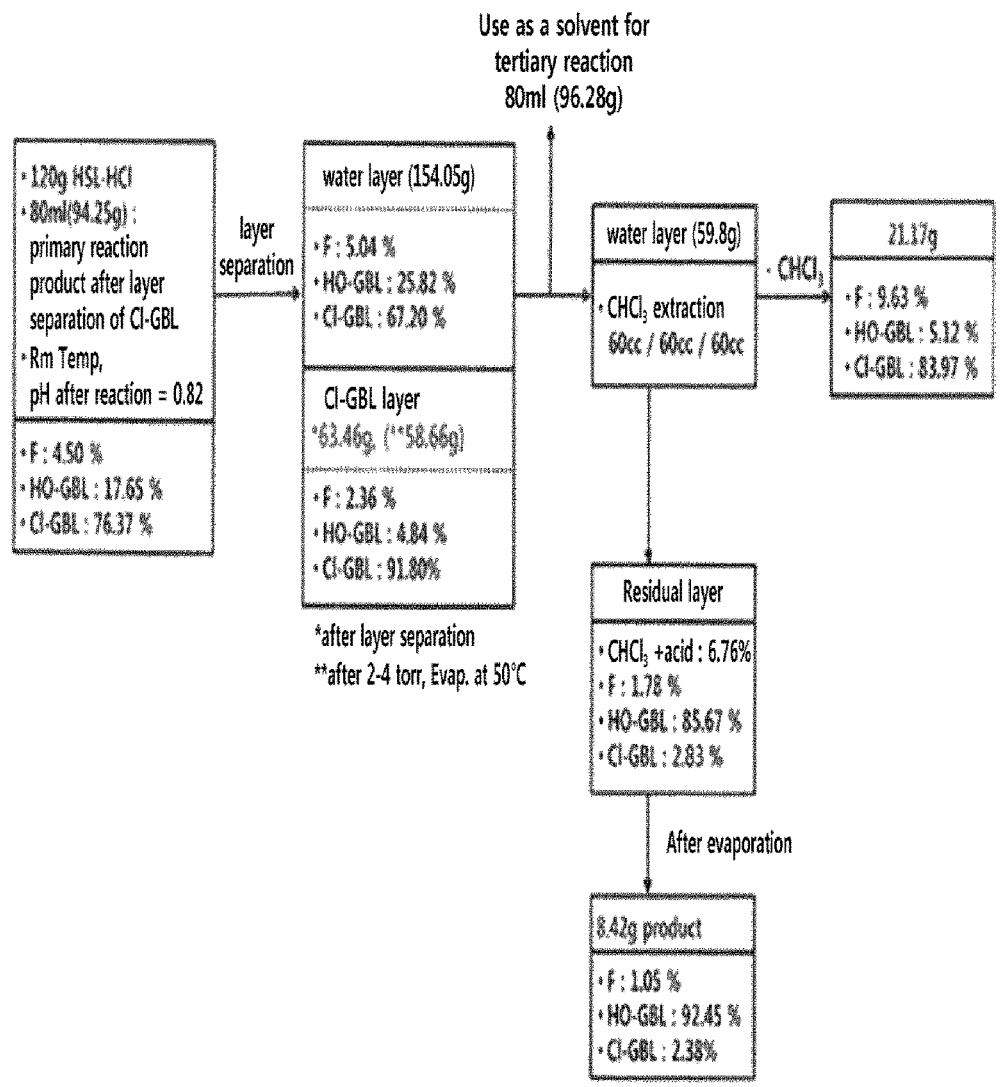

[FIG. 5]
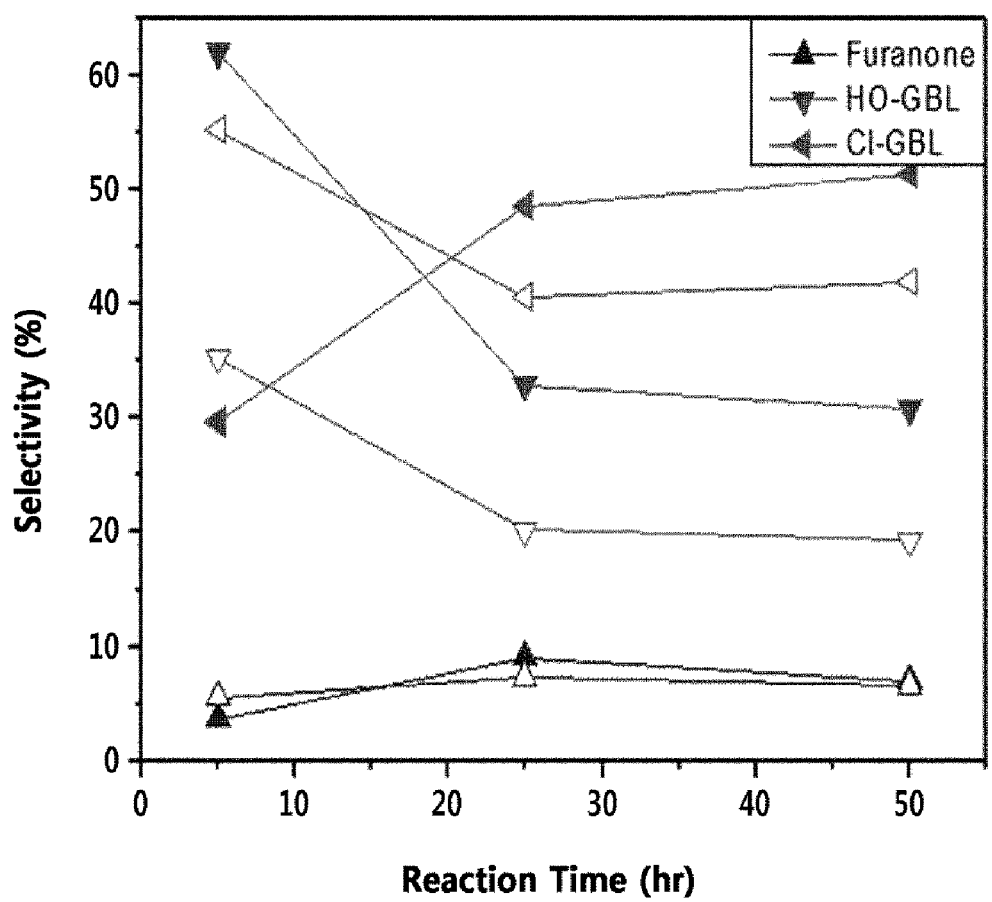

[FIG. 6]
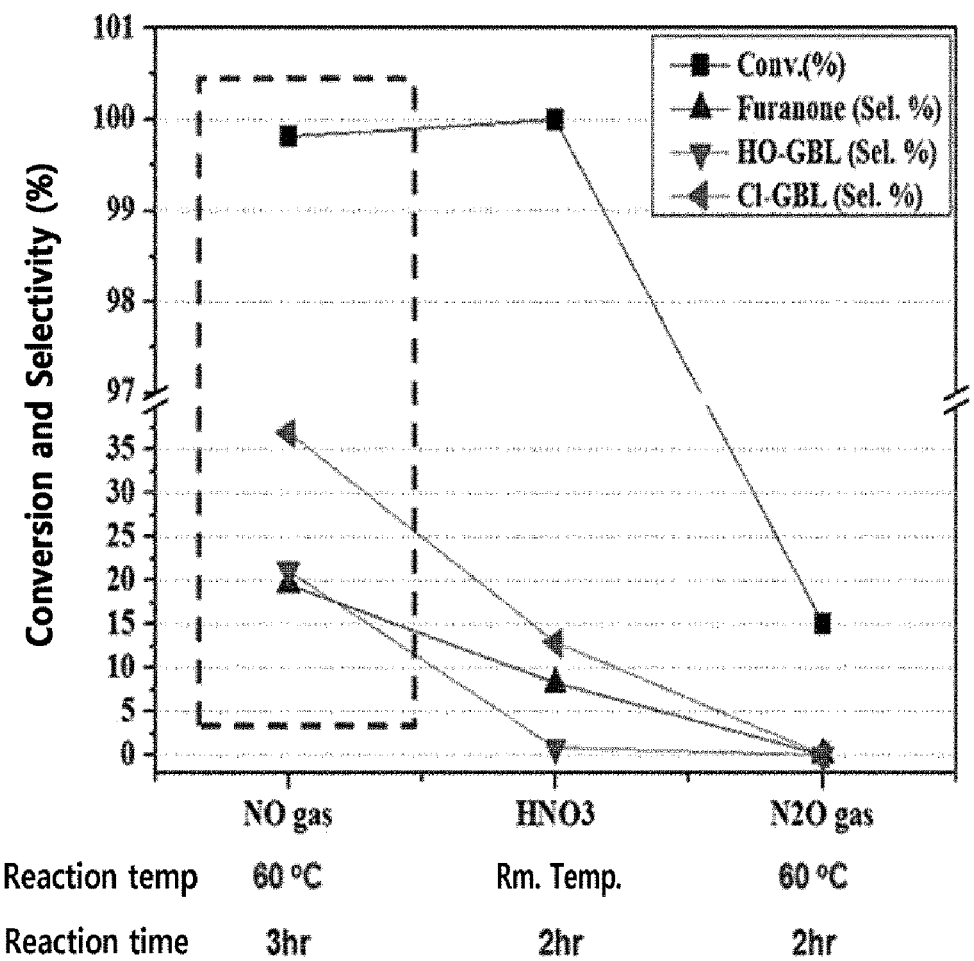

[FIG. 7]
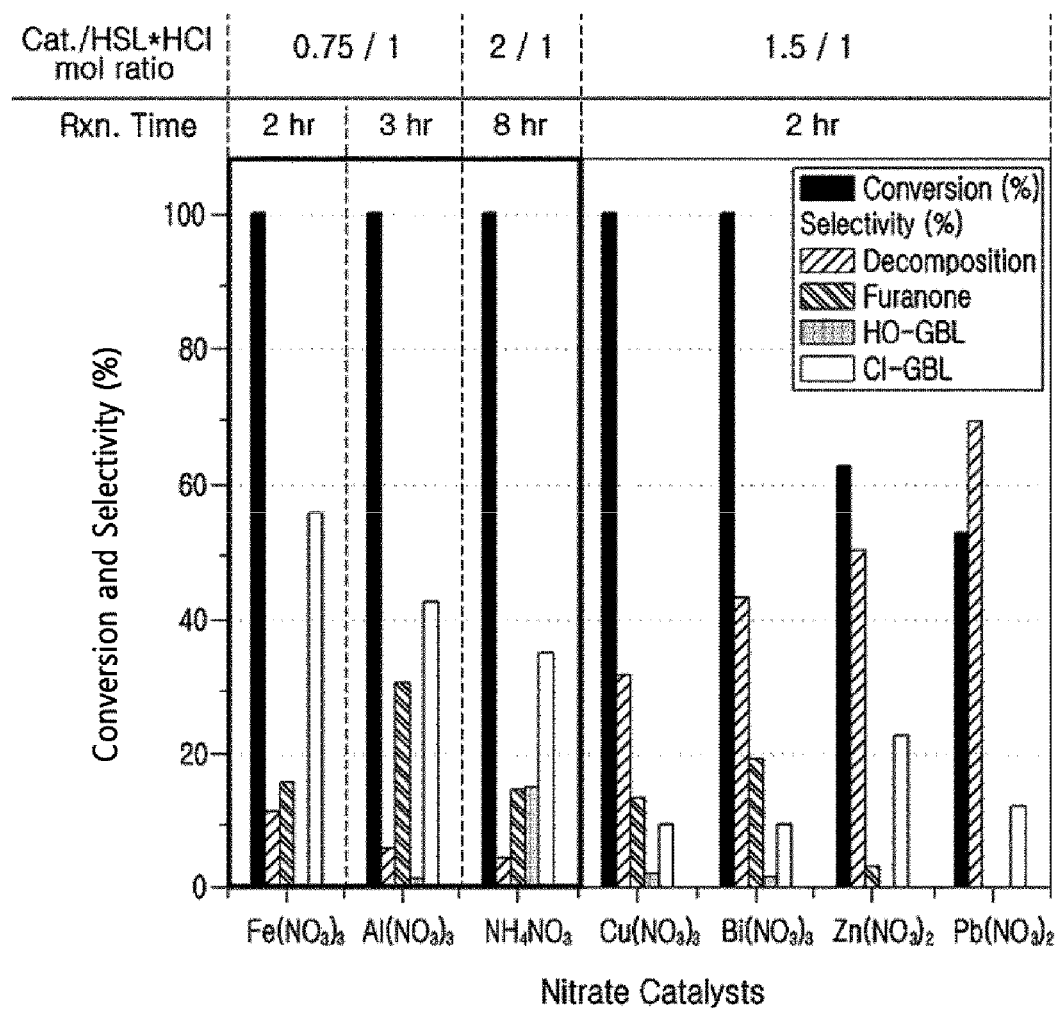

[FIG. 8]
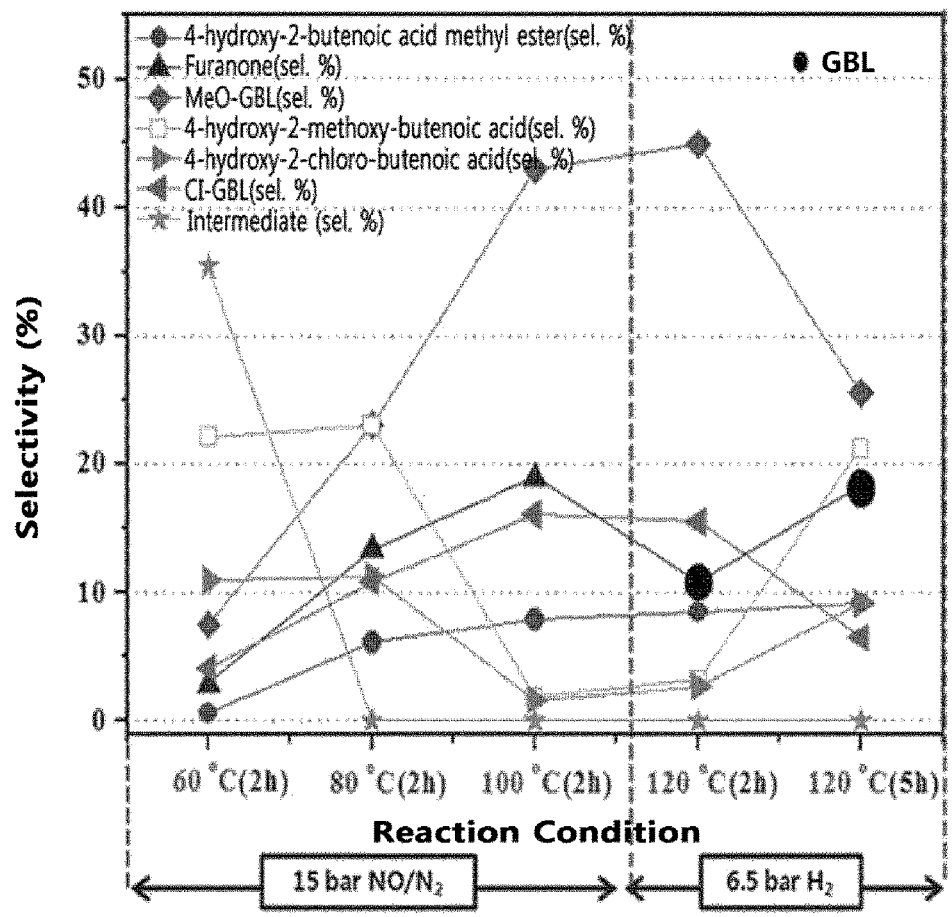

[FIG. 9]
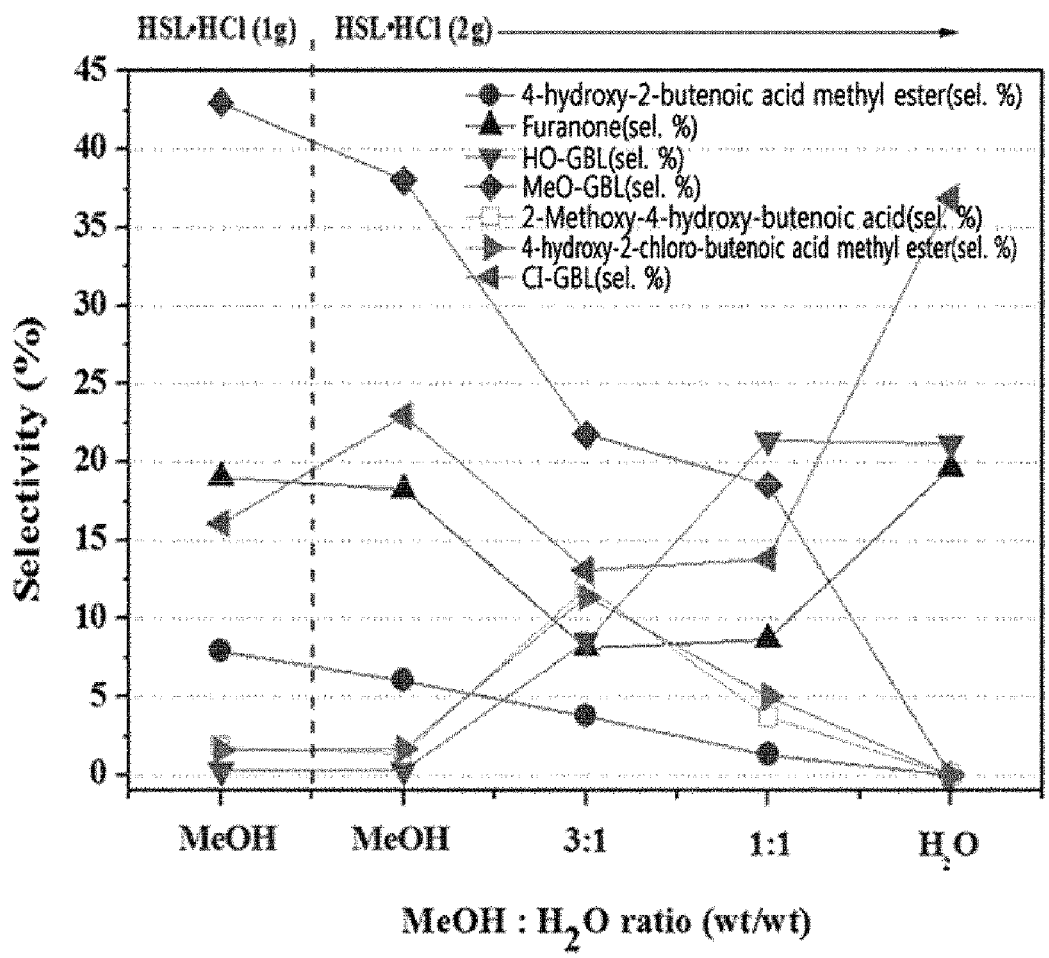

[FIG. 10]
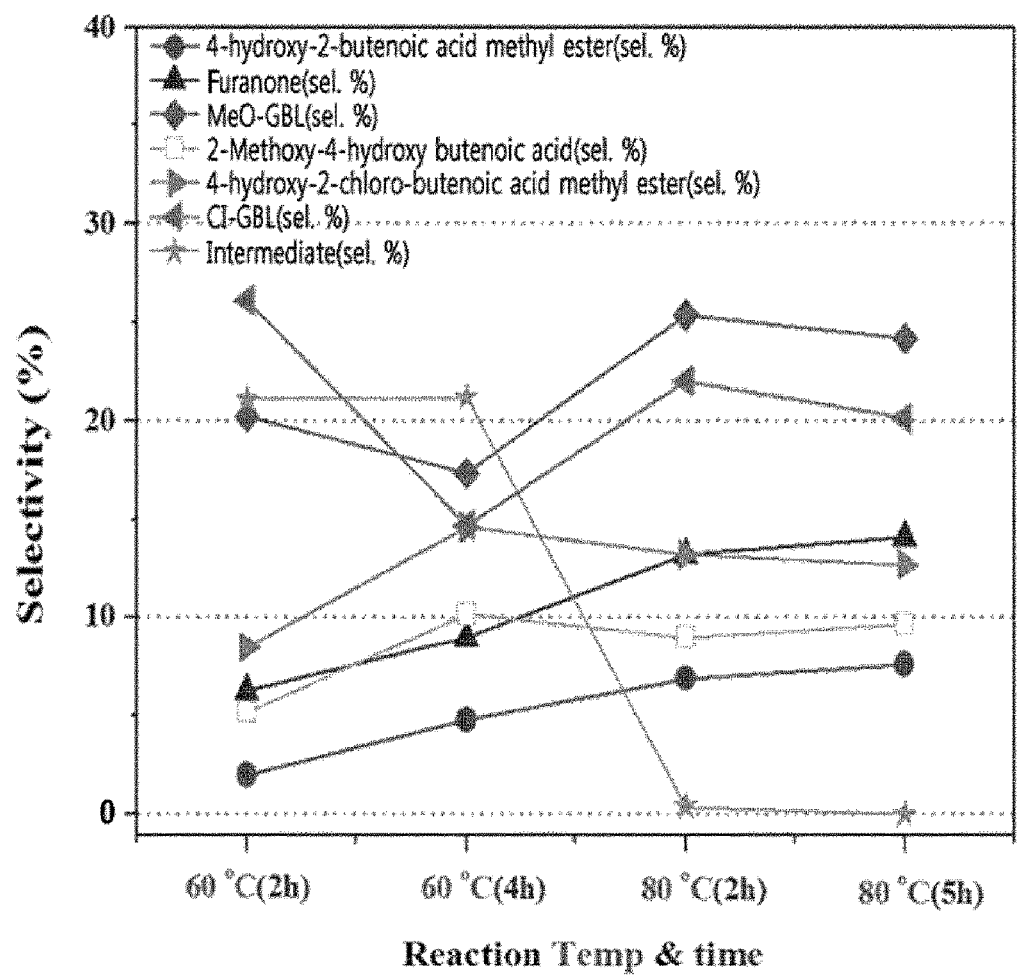

[FIG. 11]
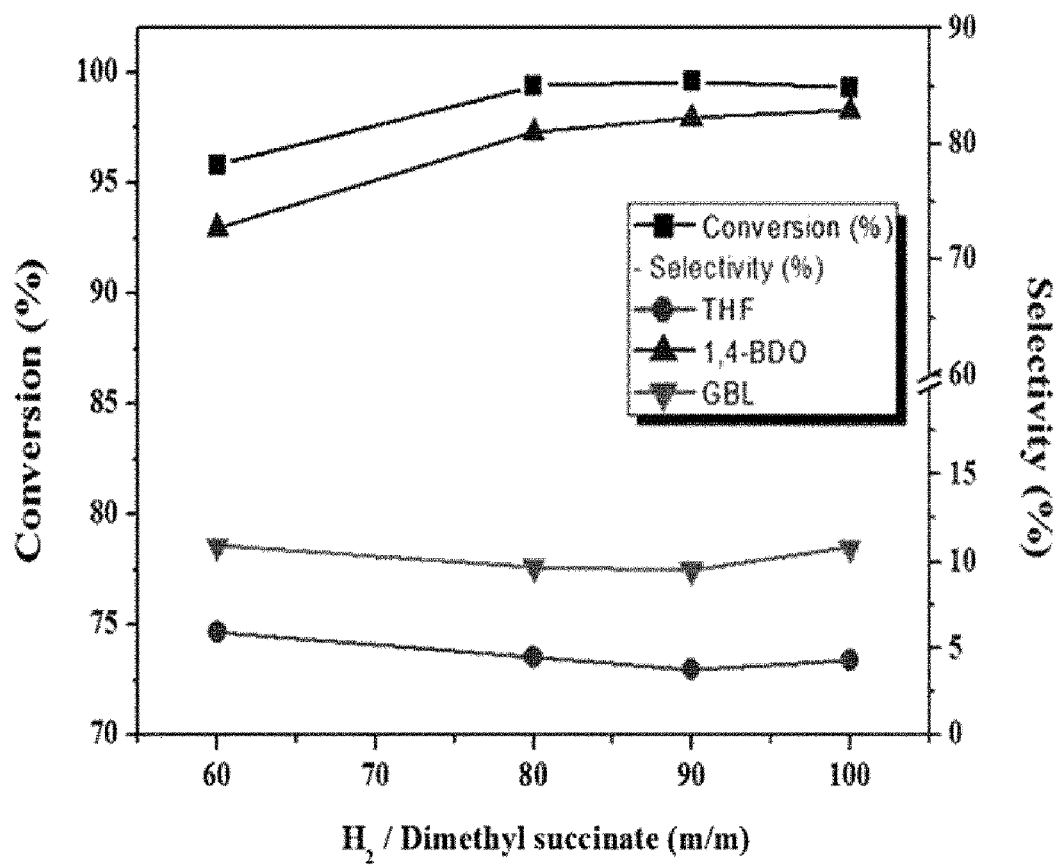

[FIG. 12]
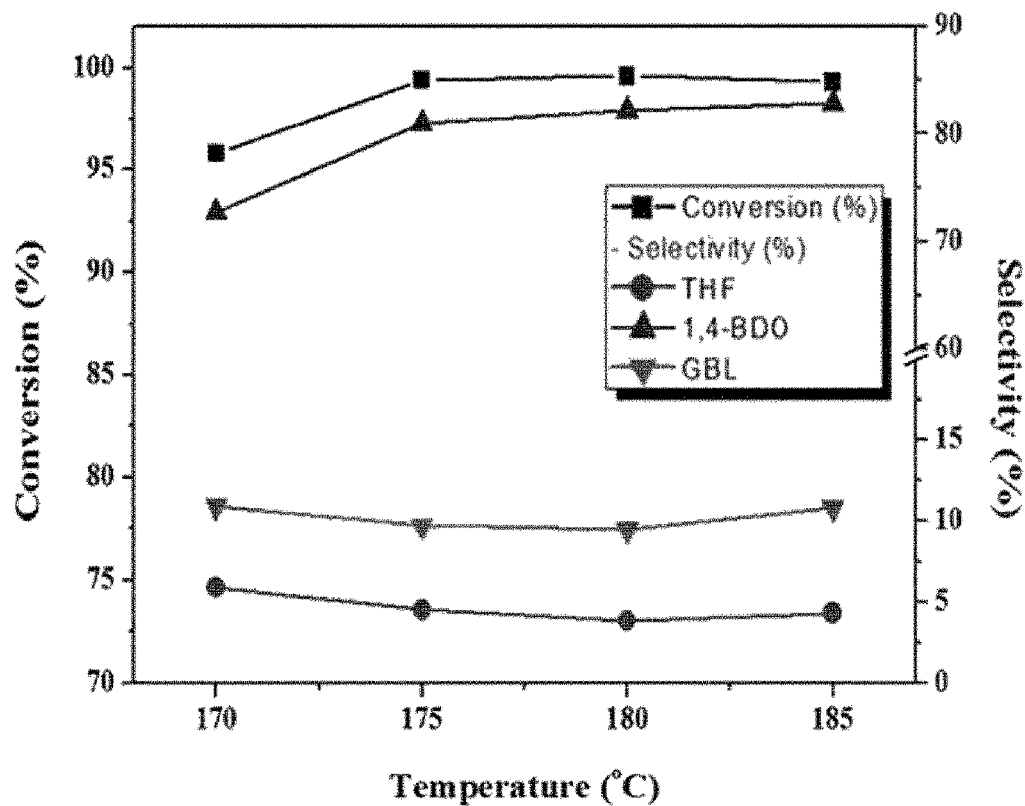

[FIG. 13]
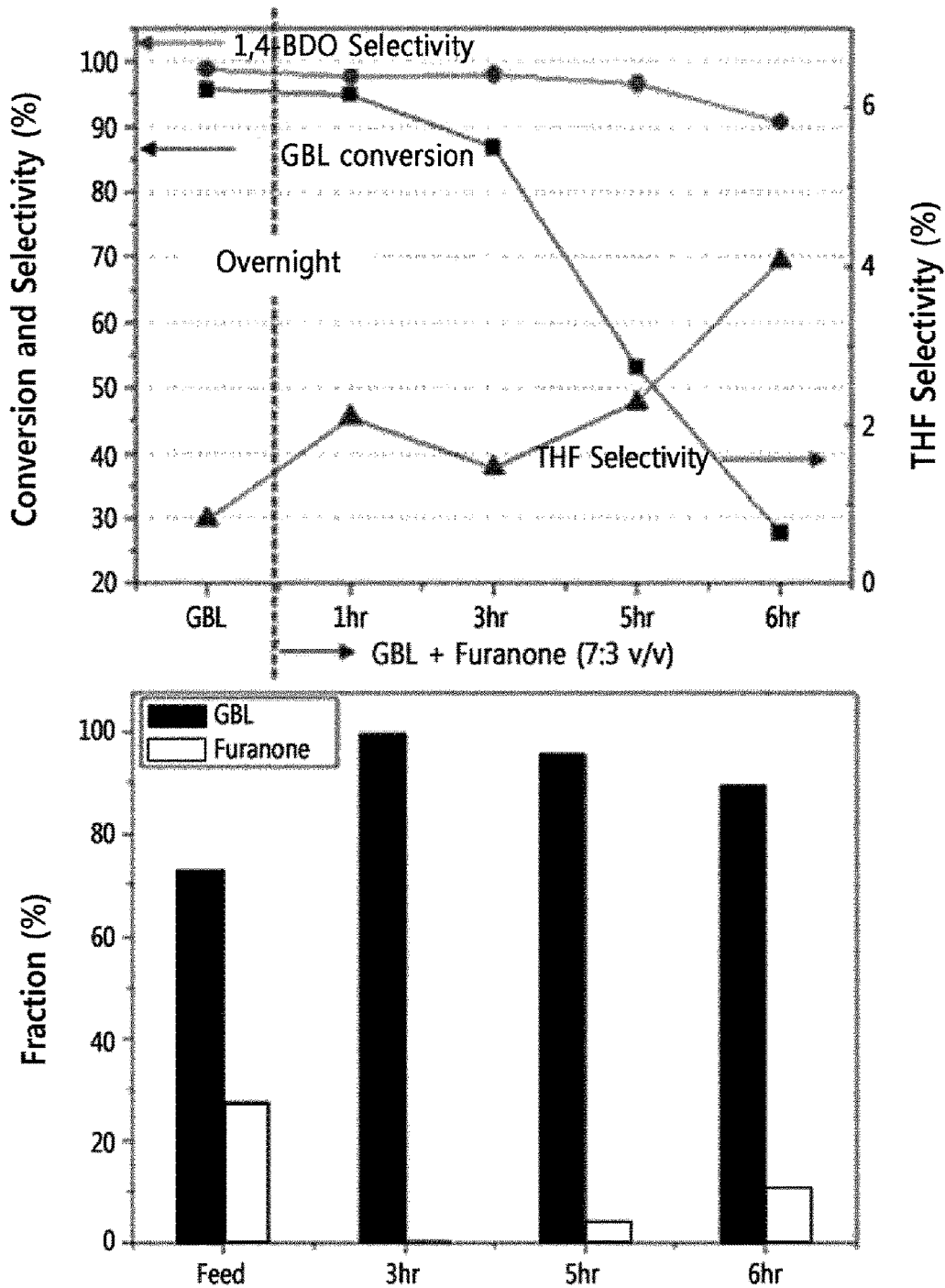

[FIG. 14]
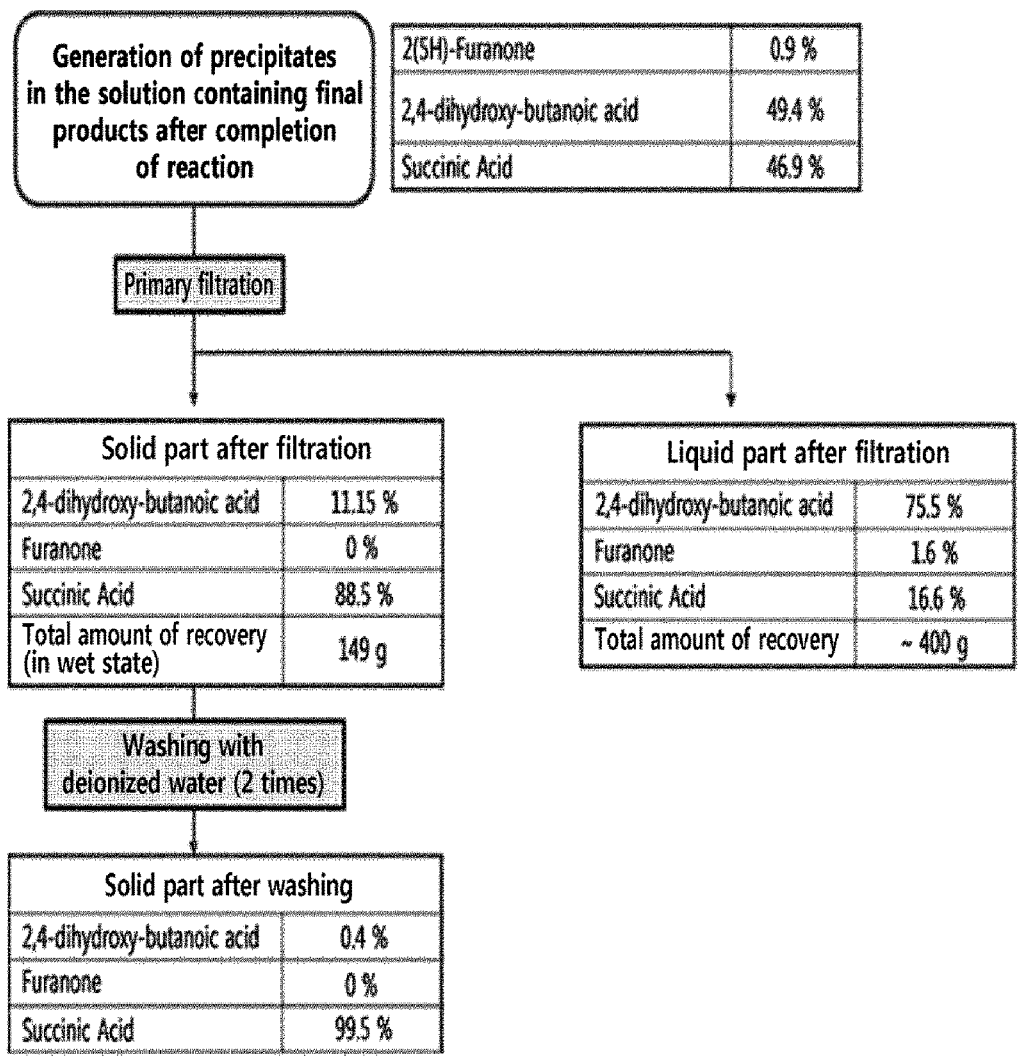

[FIG. 15]
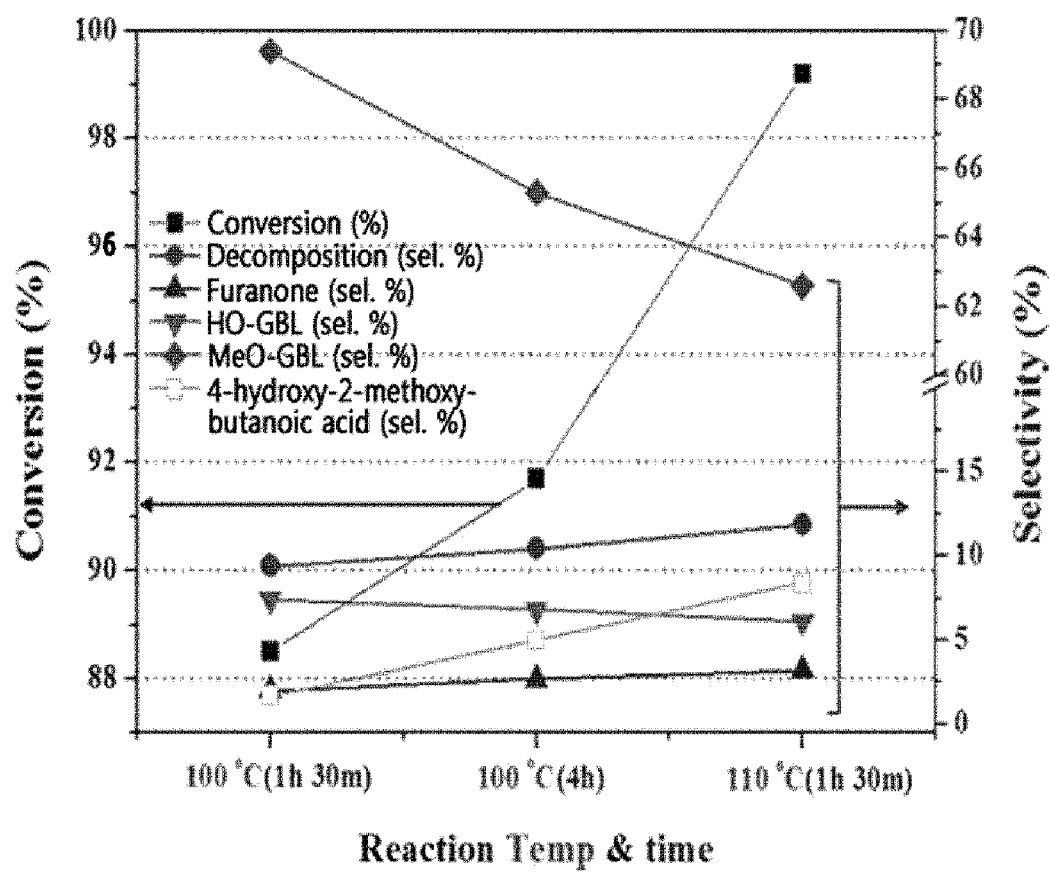

[FIG. 16]
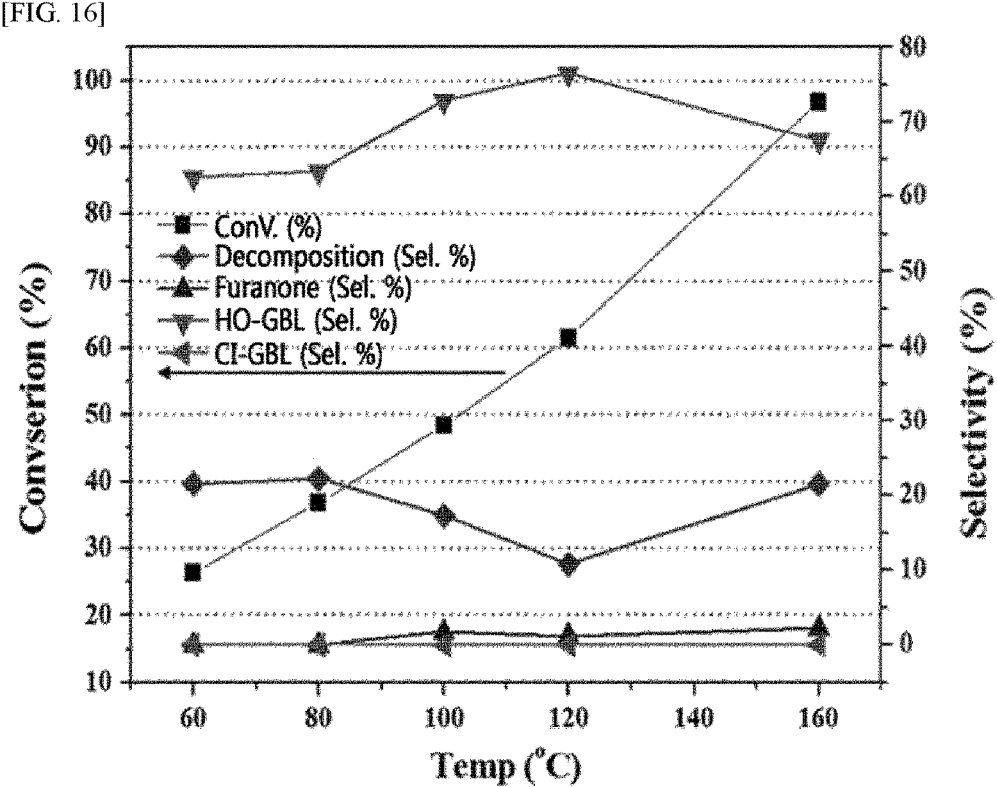

PROCESS FOR TREATING HOMOSERINE-BASED COMPOUND

CROSS-REFERENCES TO RELATED APPLICATIONS

This application is a U.S. national phase application of International PCT Patent Application No. PCT/KR2015/003635, which was filed on Apr. 10, 2015, which claims priority to Korean Patent Application Nos. 10-2014-0043860, filed Apr. 11, 2014. These applications are incorporated herein by reference in their entireties.

TECHNICAL FIELD

The present disclosure relates to a process for treating homoserine-based compounds, enabling large-scale production of useful compounds from the homoserine-based compounds.

BACKGROUND ART

Coal and petroleum, which are major natural resources in the industry, are used as raw materials for the synthesis of various compounds, while also being used as fossil fuels. In particular, distillation of petroleum can produce various materials such as alkanes, alkenes, etc., and these materials can be used as synthetic raw materials for the synthesis of various materials. For example, various materials such as polymers, drugs, and food additives are synthesized from petroleum. However, there are problems in that carbon dioxide and harmful materials are produced during the process of petroleum consumption and that the world's petroleum reserves are limited.

Accordingly, studies have focused on the substitution of petroleum as a synthetic raw material, and in particular, biomass has been highlighted among the studies. Biomass refers to a material that can be prepared from plants, for example, renewable plant resources such as corn, bean, and sugar cane, by a chemical or biological method.

Specifically, saccharides (e.g., glucose, fructose, etc.) can be obtained from plants such as sugar cane. The thus-obtained saccharides can be used as foods, and various compounds, e.g., homoserine-based compounds, can be obtained by fermenting the saccharides using microorganisms. Homoserine is an amino acid having the structure of 2-amino-4-hydroxybutanoic acid, and can be used as an intermediate for the preparation of methionine, threonine, isoleucine, etc. Homoserine can be converted into a lactone form or the 4-hydroxy moiety of homoserine can be substituted, for example, the structures of homoserine, homoserine lactone, O-acetylhomoserine, O-succinyl homoserine, homoserine lactone hydrochloride (HCl), homoserine lactone hydrobromide, etc., are possible.

For enhancing the added value of the homoserine-based compounds, gamma-butyrolactone or derivatives thereof, furanone, dialkyl succinate, etc. may be prepared by lactonization or hydrolysis. For this purpose, a process of removing an amine group from the homoserine-based compounds, i.e., a deamination process, is necessary.

As methods for performing the deamination process by an industrial chemical process, a method of using a catalyst, a method of using an enzyme, etc. have been suggested. However, the effect of the method of using a catalyst has not been confirmed and the method of using an enzyme is not suitable for large-scale industrial production.

In particular, gamma-butyrolactone is an important intermediate used for the preparation of a N-pyrrolidone derivative, which is used as an intermediate for the synthesis of polymers, pharmaceuticals, etc., and there is a growing demand for gamma-butyrolactone. Gamma-Butyrolactone can be prepared by dehydrogenation of 1,4-butanediol or hydrogenation of maleic anhydride or succinic anhydride in a petrochemical process. However, the above methods have problems in that the production cost may increase due to the significant fluctuation in the price of raw materials, and thus there is a need for the development of a new material to be used for the preparation of gamma-butyrolactone.

On the other hand, 1,4-butanediol is widely used in the industry, and in particular, it is a very important material used as a synthetic raw material for the synthesis of polybutylene terephthalate resin, polyurethane, gamma-butyrolactone, tetrahydrofuran, etc. 1,4-Butanediol is mainly prepared by a petrochemical process, and for example, it may be produced from acetylene, butadiene, propylene oxide, maleic anhydride, etc. However, it has drawbacks in that the production cost may increase due to the fluctuating price of raw materials and that its manufacturing process is complex and requires a huge facility. Accordingly, there is a need for the development of a process for preparing 1,4-butanediol from raw materials other than the petroleum-dependent raw materials.

Under these circumstances, the present inventors have made many efforts to find a process for preparing useful compounds from the homoserine-based compounds, which can be used as intermediates for preparing important compounds in the industry. As a result, they have discovered a process for treating homoserine-based compounds which is advantageous in the large-scale industrial production due to the simple process and high yield, thereby completing the present disclosure.

DISCLOSURE

Technical Problem

The present disclosure relates to the preparation of useful compounds from homoserine-based compounds, which can be used as intermediates for the preparation of important compounds in the industry, and specifically, relates to a process of treating homoserine-based compounds, by which useful compounds can be produced from the homoserine-based compounds on a large scale, and compounds produced therefrom.

Technical Solution

In order to achieve the above objects, the present disclosure provides a process for preparing gamma-butyrolactone, a gamma-butyrolactone derivative, furanone, dialkyl succinate, a by-product, or a mixture thereof, comprising:

reacting a solution of a homoserine-based compound with $NO_x$ (Step 1); and recovering gamma-butyrolactone, a gamma-butyrolactone derivative, furanone, dialkyl succinate, a by-product, or a mixture thereof from the products in Step 1 (Step 2).

Step 1 is the process of deamination of a homoserine-based compound, in which the amino group in the homoserine-based compound is removed by reacting with $NO_x$.

Examples of the homoserine-based compound may include homoserine, homoserine lactone, O-acetylhomoserine, O-succinyl homoserine, homoserine lactone hydrochloride (HCl), homoserine lactone hydrobromide, and a mixture thereof, and the structures for each of the compounds are shown below.

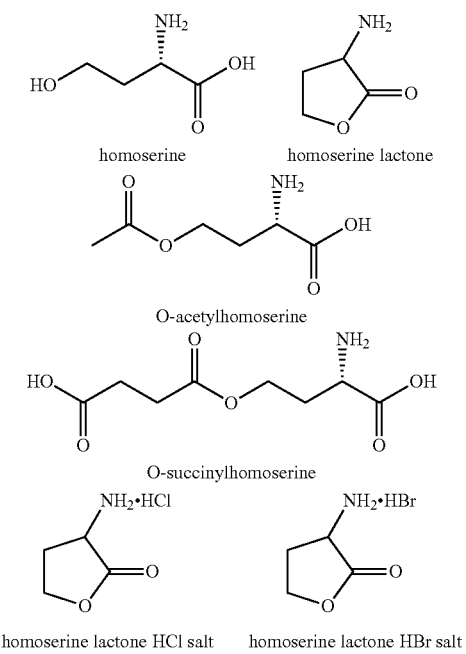

The above homoserine-based compounds have an amine group, and in the present disclosure, they are reacted with $NO_x$ to remove the amine group(s) in the compounds. As used herein, the term "$NO_x$" refers to a nitrogen oxide and is used as an oxidizing agent in the present disclosure. In $NO_x$, x refers to 1, 1.5, 2, or 3. In the present disclosure, examples of $NO_x$ may include $NO$, $N_2O_3$, $NO_2$, and $NO_3$.

$NO_x$ may directly react in the form of a gas or react in the form of an acid or salt with a homoserine-based compound. When $NO_x$ is used in the form of acid or salt, it may act as a catalyst by binding to $HNO_3$, $NH_4NO_3$, or a metal ion. For example, $NO_x$ may act in the form of $NaNO_2$, $Fe(NO_3)_3$, $Al(NO_3)_3$, $Cu(NO_3)_3$, $Bi(NO_3)_3$, $Zn(NO_3)_2$, or $Pb(NO_3)_2$.

When $NO_x$ is used in the form of a gas, NO gas will be used alone thus enabling deamination. Additionally, $NO_x$ may be used in NO gas in combination with O2 gas, an inert gas, or a mixture thereof, or may be used along with a catalyst. The inert gas to be used may include $N_2$ gas, He gas, Ar gas, or a mixture thereof.

Additionally, when NO gas is used along with $O_2$ gas, NO reacts with $O_2$ to form $NO_2$, $N_2O_3$, etc., and these can be used for deamination along with NO. The NO gas and the $O_2$ gas may be used in a molar ratio of 1 to 3:1 ($NO:O_2$), and specifically 2:1. The $O_2$ gas may also be used as air.

In a closed reaction system, an inert gas may be used together for the purpose of increasing a reaction pressure. Additionally, in an open reaction system, it may be to use NO or $O_2$, which does not include an inert gas. Additionally, in an open reaction system, an inert gas may be used simultaneously, however, the increase of the amount of the gas being supplied may shorten the contact hours between reactants with the gas, thereby causing a loss of the NO gas. Accordingly, it may be to use pure NO gas which does not include an inert gas.

For reacting with NO or $NO_x$, and a homoserine-based compound, the homoserine-based compound may be used in the form of a solution or in a state dispersed in a solvent. Specifically, examples of the solvent of the homoserine-based compound may include a solvent in which the homoserine-based compound can be dissolved or swollen, or a solvent which has a high absorbent concentration of NO or $NO_x$ gas. In another aspect, a solvent which can mediate easy separation of a product may be used. According to the selectivity of a product, the solvent may be water, chloroform, dichloroform, methanol, halo-gamma-butyrolactone, or a mixture thereof.

Among the products produced by deamination, the selectivity of gamma-butyrolactone derivatives varies according to the selection of the solvent for the homoserine-based compound. For example, when water is used as a solvent, the production of hydroxy-gamma-butyrolactone is promoted, whereas when an organic solvent such as chloroform, dichloroform, halo-gamma-butyrolactone, or a mixture thereof is used, the production of hydroxy-gamma-butyrolactone becomes minimized. Additionally, when methanol is used as a solvent, methoxy-gamma-butyrolactone is produced.

According to the homoserine-based compound being used, various products are produced. Specifically, when homoserine lactone is used, hydroxy-gamma-butyrolactone is produced overwhelmingly, whereas when a homoserine lactone salt is used, halo-gamma-butyrolactone is produced overwhelmingly. Furanone is produced along with other compounds, regardless of the kinds of homoserine derivatives. When O-succinyl homoserine or O-acetylhomoserine is used, 2,4-dihydroxybutanoic acid is produced and succinic acid, succinic anhydride, acetic acid, and acetic anhydride are produced. In this regard, a further esterification may be performed using an alcohol to prepare dialkyl succinate. Acetoxy-gamma-butyrolactone may be prepared by subjecting hydroxy-gamma-butyrolactone to a further acetylation with acetic acid, acetic anhydride, or acetyl chloride. In Step 1, in particular, when a homoserine lactone salt is a reactant and water or a halo-gamma-butyrolactone derivative is used as a solvent, a layer separation of a product(s) due to the difference in specific gravity and solubility during deamination occurs. Accordingly, unreacted materials and product(s) can be easily separated and recovered.

Additionally, a halide may be added in order to increase the selectivity of halo-gamma-butyrolactone among the products. More specifically, when a homoserine lactone salt is used for deamination, it may be to add the same halide which is forming the homoserine lactone salt in order to maximize the selectivity. The halide is specifically hydrobromic acid, hydrochloric acid, hydrofluoric acid, or hydroiodic acid, and the addition of the halide may increase the production rate of the gamma-butyrolactone substituted with a halogen. Without wishing to be bound by theory, a halogen in a halide may be partially involved in the reaction during the process of reacting a homoserine-based compound and $NO_x$, thereby increasing the production rate of the gamma-butyrolactone substituted with a halogen. Additionally, it is may be to use chloroform, dichloroform, and halo-butyrolactone, which do not contain water, for minimizing the amount of hydroxy-gamma-butyrolactone produced when a solvent is used.

Additionally, in Step 1, the reaction may be performed without a catalyst, or a metal catalyst may be used. The metal catalyst can accelerate the reaction between $NO_x$, specifically NO gas which does not use $O_2$, and a homoserine-based compound. The metal catalyst may be added to the reaction system of Step 1 or a solution of a homoserine-based compound. The metal catalyst may be at least one selected from $M_1/X$, $M_1M_2/X$, and $Fe_2O_3$, in which $M_1$ and $M_2$ are not the same as each other and are a noble metal or a transition metal, and X is activated carbon or $SiO_2$. More preferably, the noble metal may be Pd, Pt, Rh, Ir, Re, Ru, or Au, and the transition metal may be Fe, Pb, Sb, Ag, Al, Cu, Ni, Cr, or Zn.

Additionally, the reaction temperature in Step 1 may be at 0° C. to 200° C. Additionally, the reaction pressure in Step 1 may be 1 atm to 100 atm. The reaction pressure may be controlled by a gas being supplied (e.g., NO, an inert gas, etc.).

In an exemplary embodiment, in Step 1, when deamination is performed using NO gas without using $O_2$, the reaction may be performed at 50° C. to 150° C. Additionally, the reaction pressure may be in the range of 5 atm to 50 atm. The reaction pressure may be controlled by a gas being supplied (e.g., NO, an inert gas, etc.).

In another exemplary embodiment, in Step 1, when NO gas is used alone or both NO gas and $O_2$ gas are used simultaneously, the reaction may be performed at 0° C. to 50° C. Additionally, the reaction pressure may be 1 atm, but is not particularly limited thereto.

Step 2 relates to separation and recovery of gamma-butyrolactone, a gamma-butyrolactone derivative, furanone, dialkyl succinate, a by-product, or a mixture thereof, which were prepared from the homoserine-based compound in Step 1.

In the above products, the gamma-butyrolactone derivative may be halo-gamma-butyrolactone, hydroxy-gamma-butyrolactone, methoxy-gamma-butyrolactone, acetoxy-gamma-butyrolactone, or a mixture thereof. The by-products may be succinic acid, succinic anhydride, acetic acid, acetic anhydride, 2,4-dihydroxybutanoic acid, 4-hydroxy-2-butenoic acid methyl ester, 4-hydroxy-2-methoxybutanoic acid, 4-hydroxy-2-chloro butanoic acid, or a mixture thereof. Additionally, the by-product may be recycled to be used for the purpose of increasing the selectivity of products in the process of the present disclosure after separation and recovery.

Each of the compounds produced from the above products may be separated by the conventional separation method, e.g., distillation, etc.

Additionally, each product may be separated and recovered by the method described below for the efficiency of the process, according to the homoserine-based compound used in Step 1.

In an exemplary embodiment, when the reactant in Step 1 is homoserine lactone hydrochloride or homoserine lactone hydrobromide, each product may be separated and recovered as described below.

When the reactant in Step 1 is homoserine lactone hydrochloride or homoserine lactone hydrobromide, halo-gamma-butyrolactone and hydroxy-gamma-butyrolactone can be obtained as main products. Halo-gamma-butyrolactone and hydroxy-gamma-butyrolactone can be recovered and separated from the lower layer in high yield due to the difference in specific gravity and solubility.

Additionally, the solution containing the products in Step 1 may be extracted using an organic solvent such as chloroform, dichloroform, methyl chloroform, or tetrachloroethane, thereby recovering halo-gamma-butyrolactone or hydroxy-gamma-butyrolactone. It may be to separate and recover the lower layer and then extract the upper layer using an organic solvent as described above. This is because the above extraction can be easily performed by first separating the lower layer by layer separation to recover halo-gamma-butyrolactone first.

As an alternative, specifically, the lower layer is separated and recovered from the products, and then a part in the upper layer is returned to Step 1 to be used as a reaction solvent, and the remaining part in the upper layer is extracted as described above. That is, the process efficiency can be increased by recycling the acids (HCl, HBr, etc.) and $NO_x$ contained in the solution of the deamination product present in the upper layer and re-using the solution having a relatively increased fraction of hydroxy-gamma butyrolactone due to the removal of halo-butyrolactone thereby enabling the preparation of halo-gammabutyrolactone as a main product. Additionally, the costs for treating wastewater and the costs incurred due to the use of NO gas and a halide (HCl, HBr, etc.) can be reduced by minimizing the amount of the solvent used in the entire process.

Additionally, the residual solution after the recovery of the halo-gamma-butyrolactone or hydroxy-gamma-butyrolactone can be recycled into Step 1. The recycling has an advantage in that the unreacted materials present in the residual solution can be recycled again into Step 1, thereby increasing the process efficiency, and also the amount of the solvent used in the entire process can be minimized because the residual solution contains a large amount of the solvent for the homoserine-based compound in Step 1. Alternatively, hydroxy-gamma-butyrolactone, furanone, or a mixture thereof can be recovered from the residual solution. Since the residual solution is in a state where the halo-gamma-butyrolactone is maximally removed, hydroxy-gamma-butyrolactone, furanone, or a mixture thereof can be recovered by removing the solvent contained in the residual solution. The solvent may be removed by a conventional method, e.g., distillation, heating, etc.

In another exemplary embodiment, when the reactant in Step 1 is O-succinylhomoserine, each of the products may be separated and recovered as follows.

When the reactant in Step 1 is O-succinylhomoserine, a hydrolysis reaction of O-succinylhomoserine occurs concurrently with the deamination of O-succinylhomoserine, thereby producing succinic acid or succinic anhydride and 2,4-dihydroxy-butanoic acid as primary products while producing succinic acid or succinic anhydride as a precipitate. A part of succinic acid and succinic anhydride is recovered by filtration, in which the solvent is removed from the solution containing succinic acid, succinic anhydride, and 2,4-dihydroxy-butanoic acid by distillation under reduced pressure, and esterification is performed with methanol, thereby converting succinic acid or succinic anhydride into dialkyl succinate. The solvent removal and the acid added during the esterification reaction cause the cyclodehydration of 2,4-dihydroxy-butanoic acid, thereby forming hydroxy-gamma-butyrolactone. Succinic acid (b.p.: 235° C.), succinic anhydride (b.p.: 261° C.), hydroxy-gamma-butyrolactone (b.p.: 249.3° C.), and dimethyl succinate (b.p.: 195.3° C.) may be subjected to distillation under reduced pressure to be recovered as main products.

In still another exemplary embodiment, when the reactant in Step 1 is homoserine, each of the products may be separated and recovered as follows.

When the reactant in Step 1 is homoserine, 2,4-dihydroxy-butanoic acid and succinic acid are produced first as main products. Then, 2,4-dihydroxy-butanoic acid is subjected to cyclodehydration and converted into hydroxy-gamma-butyrolactone, and subsequently dimethyl succinate is recovered as a main product by an esterification reaction of succinic acid. Then, hydroxy-gamma-butyrolactone can be recovered by removing the solvents and by-product with relatively low boiling points via distillation.

In still another exemplary embodiment, when the reactant in Step 1 is acetyl-homoserine, each of the products may be separated and recovered as follows.

When the reactant in Step 1 is acetyl-homoserine, 2,4-dihydroxy-butanoic acid and acetic acid or acetic anhydride are produced first as main products, and hydroxy-gamma-butyrolactone, acetoxy-gamma-butyrolactone, or a mixture thereof may be obtained as final products. Depending on whether the target product is hydroxy-gamma-butyrolactone or acetoxy-gamma-butyrolactone, only a purification step may be performed alone or acetylation may be performed as well. When the target product is hydroxy-gamma-butyrolactone, it may be recovered by removing acetic acid, acetic anhydride, solvents, and impurities with low boiling points. In contrast, when the target product is acetoxy-gamma-butyrolactone, the produced 2,4-dihydroxybutanoic acid is subjected to cyclodehydration, and further to acetylation with acetic acid and acetic anhydride contained in the solution, and the impurities with low boiling points are removed to thereby recover acetoxy-gamma-butyrolactone.

Additionally, the present disclosure may further comprise reacting halo-gamma-butyrolactone or hydroxy-gamma-butyrolactone among the gamma-butyrolactone derivatives recovered in Step 2 with hydrogen in the presence of a hydrogenation catalyst, thereby converting them into gamma-butyrolactone, furanone, or a mixture thereof (Step 3).

Step 3 is a hydrogenation reaction, in which halogen and hydroxy moiety are removed from the halo-gamma-butyrolactone and the hydroxy-gamma-butyrolactone by a hydrogenation catalyst, respectively, and thereby gamma-butyrolactone or furanone may be prepared. Other by-products, at least one selected from the group consisting of 4-halo-butyric acid, 3-halopropanol, butyric acid, THF, 2-HO-THF, 1-PrOH, 2-PrOH, 1-BuOH, and 2-BuOH, may also be prepared.

The hydrogenation catalyst may be used as a catalyst for dechlorination or a catalyst for dehydrogenation-dehydration, in which the hydrogenation catalyst may be at least one selected from $M_1/X_1$, $M_1M_2/X_1$, $M_1/X_1X_2$, and $M_1M_2/X_1X_2$. In particular, $M_1$ and $M_2$ are not the same as each other and are a noble metal or a transition metal, and each of $X_1$ and $X_2$ is activated carbon or a metal oxide. Preferably, the noble metal may be Pd, Pt, Rh, Ir, Re, Ru, or Au, and the transition metal may be Fe, Pb, Sb, Ag, Al, Cu, Ni, Cr, In, W, P, Te, or Zn. Additionally, $X_1$ and $X_2$ are not the same as each other and are activated carbon or a metal oxide. The metal oxide may be a mixed metal oxide containing a material selected from the group consisting of Al, Zr, Si, and Ti, and the metal oxide may be chemically modified, and an inorganic acid ($PO_4$, $SO_4$) may be used in this regard. In the case of a metal oxide, in which $X_1$ and $X_2$ in the hydrogenation catalyst are chemically modified, furanone is mainly produced as the product of hydrogenation.

Step 3 may be performed in the presence of at least one solvent selected from the group consisting of dioxane, gamma-butyrolactone, halo-gamma-butyrolactone, hydroxy-gamma-butyrolactone, diethylene glycol, dimethyl ether, dimethyl sulfoxide, and propylene carbonate. Step 3 is a hydrogenation reaction, which can be performed under the conventional reaction conditions in the art, and preferably, in the range of 100° C. to 400° C., and 1 atm to 30 atm.

Additionally, the present disclosure may further comprise reacting hydroxy-gamma-butyrolactone among the gamma-butyrolactone derivatives recovered in Step 2 with acetic acid, acetic anhydride, or acetyl chloride, thereby converting it into acetoxy-gamma-butyrolactone (Step 4); and heating the acetoxy-gamma-butyrolactone, thereby converting it into gamma-butyrolactone, a by-product, or a mixture thereof (Step 5).

Step 4 is a reaction for substituting the hydroxy group of hydroxy-gamma-butyrolactone into an acetoxy group, and hydroxy-gamma-butyrolactone can be converted into acetoxy-gamma-butyrolactone by reacting with acetic acid, acetic anhydride, or acetyl chloride. The reaction may be performed under heat reflux, and the reaction may be performed at a temperature of 80° C. to 150° C., under a pressure of 5 torr or less. Additionally, an additional catalyst may be used to reduce the reaction temperature (e.g., resin; Amberyst-35dry).

Step 5 is a deacetoxylation reaction, in which the acetoxy-gamma-butyrolactone prepared in Step 4 can be converted into gamma-butyrolactone, furanone, a by-product, or a mixture thereof by heat treatment. The acetoxy group of the acetoxy-gamma-butyrolactone may be removed by the heat treatment, and the reaction temperature is may be in the range of 400° C. to 600° C. Additionally, the heat treatment may further produce furanone, and may progress further to produce by-products. The by-products are acrolein, butyl acetate, halo-gamma-butyrolactone, or a mixture thereof. Additionally, the removal of the acetoxy group may cause production of acetic acid and the acetic acid may be recovered to be recycled into Step 4. Additionally, halo-gamma-butyrolactone corresponds to a gamma-butyrolactone derivative, and thus it can be separated and recovered to be used for recycling.

Additionally, the present disclosure may further comprise reacting the gamma-butyrolactone or furanone, which was prepared in Step 2, Step 3, or Step 5, with hydrogen in the presence of a metal catalyst, thereby converting it into 1,4-butanediol (Step 6).

Step 6 is a ring-opening reaction, in which gamma-butyrolactone or furanone can be converted into 1,4-butanediol by the opening of the ring thereof. The reaction may be performed by reacting with hydrogen in the presence of a metal catalyst, and the metal catalyst is at least one selected from $M_1/X$ and $M_1M_2/X$, in which $M_1$ and $M_2$ are not the same as each other and are a noble metal or a transition metal, and X is activated carbon or a metal oxide. Preferably, the noble metal is Pd, Pt, Rh, Ir, Re, Ru, or Au, and additionally, the transition metal is preferably Fe, Pb, Sb, Ag, Al, Cu, Ni, Cr, or Zn. Additionally, the metal oxide is preferably $Al_2O_3$, $ZrO_2$, $SiO_2$, or $TiO_2$.

The reaction may be performed at a temperature of 150° C. to 200° C. Additionally, the reaction is may be performed under a pressure of 20 atm to 60 atm.

Additionally, the present disclosure may further comprise reacting the dialkyl succinate, which was prepared in Step 2, with hydrogen in the presence of a metal catalyst, thereby converting it into 1,4-butanediol (Step 7).

The reaction may be performed by reacting with hydrogen in the presence of a metal catalyst. The metal catalyst is at least one selected from $M_1/X$ and $M_1M_2/X$, in which $M_1$ and $M_2$ are not the same as each other and are a noble metal or a transition metal, and X is activated carbon or a metal oxide. Preferably, the noble metal is Pd, Pt, Rh, Ir, Re, Ru, or Au, and additionally, the transition metal is preferably Fe, Pb, Sb, Ag, Al, Cu, Ni, Cr, or Zn. Additionally, the metal oxide is preferably $Al_2O_3$, $ZrO_2$, $SiO_2$, or $TiO_2$.

The reaction may be performed at a temperature of 150° C. to 200° C. Additionally, the reaction may be performed under a pressure of 20 atm to 60 atm.

The entire preparation method according to the present disclosure is schematically illustrated in FIG. 1. As illustrated in FIG. 1, gamma-butyrolactone, a gamma-butyrolactone derivative, furanone, and dialkyl succinate can be recovered from a homoserine-based compound by Step 1 and Step 2. From each of the products, gamma-butyrolactone can be prepared by Steps 3 through 7, and finally 1,4-butanediol can be prepared.

Additionally, some steps may be omitted from the entire preparation process according to the products to be prepared, and also, steps may be omitted when the amount of a product is little.

Advantageous Effects of the Disclosure

The process for treating a homoserine-based compound according to the present disclosure can prepare a useful compound, which can be used as an intermediate for the preparation of an important compound in the industry, from a homoserine-based compound in a simple manner with excellent efficiency and thus can improve the utilization value of the homoserine-based compound.

BRIEF DESCRIPTION OF THE DRAWINGS

FIG. 1 shows a flow chart illustrating the entire process of the present disclosure.

FIGS. 2 to 4 show flow charts illustrating the processes and results of the deamination reaction of homoserine lactone hydrochloride (HCl) according to an exemplary embodiment of the present disclosure, in which FIG. 2 relates to the primary reaction, FIG. 3 to the secondary reaction, and FIG. 4 to the tertiary reaction.

FIG. 5 shows a graph illustrating the result of the deamination reaction of homoserine lactone hydrochloride (HCl) according to an exemplary embodiment of the present disclosure.

FIG. 6 shows a graph illustrating the result of the deamination reaction of homoserine lactone hydrochloride (HCl) according to an exemplary embodiment of the present disclosure.

FIG. 7 shows a graph illustrating the result of the deamination reaction of homoserine lactone hydrochloride (HCl) according to an exemplary embodiment of the present disclosure, in which the reaction result according to each catalyst is shown in graphs.

FIG. 8 shows a graph illustrating the result of the deamination reaction of homoserine lactone hydrochloride (HCl) according to an exemplary embodiment of the present disclosure.

FIG. 9 shows a graph illustrating the result of the deamination reaction of homoserine lactone hydrochloride (HCl) according to an exemplary embodiment of the present disclosure.

FIG. 10 shows a graph illustrating the result of the deamination reaction of homoserine lactone hydrochloride (HCl) according to an exemplary embodiment of the present disclosure.

FIG. 11 shows a graph illustrating the difference in reactivity according to the molar ratio of $H_2$/DMS, among the results of the preparation of 1,4-BDO from dimethyl succinate according to an exemplary embodiment of the present disclosure.

FIG. 12 shows a graph illustrating the difference in reactivity according to the reaction temperature, among the results of the preparation of 1,4-BDO from dimethyl succinate according to an exemplary embodiment of the present disclosure.

FIG. 13 shows a graph illustrating the result of the preparation of 1,4-BDO from gamma-butyrolactone and furanone according to an exemplary embodiment of the present disclosure.

FIG. 14 shows a graph illustrating the process and result of the preparation of hydroxy-gamma-butyrolactone and dimethyl succinate from O-succinylhomoserine according to an exemplary embodiment of the present disclosure.

FIG. 15 shows a graph illustrating the result of the preparation of methoxy-gamma-butyrolactone from homoserine according to an exemplary embodiment of the present disclosure.

FIG. 16 shows a graph illustrating the result of the preparation of hydroxy-gamma-butyrolactone from homoserine according to an exemplary embodiment of the present disclosure.

BEST MODE

Hereinafter, the present disclosure will be described in more detail with reference to the following examples and experimental examples. However, the following examples and experimental examples are provided for illustrative purposes only, and the scope of the present disclosure should not be limited thereto in any manner.

EXPERIMENTAL METHOD

In Examples shown below, each of the products was confirmed by gas chromatography (GC). The conditions for the gas chromatography analysis are as follows.

Column used: DB-200 (Agilent, P.N 123-2033, 30 m×0.32 mm, 0.5 μm) DB-WAX (Agilent, PN 123-7032, 30 m, 0.32 mm, 0.25 μm)

GC analysis conditions (DB-200): 100° C. (5')/7° C.·min$^{-1}$/250° C. (10')

GC analysis conditions (DB-WAX): 80° C. (5')/7° C.·min$^{-1}$/220° C. (10')

Additionally, in Tables below, the conversion was calculated as the yield of products relative to the reactants and the selectivity refers to a percentage according to the peak area of each product relative to the total products according to GC analysis. Additionally, each catalyst was represented in terms of $M_1(n_1)/X$ or $M_1(n_1)M_2(n_2)/X$, in which each of $M_1$ and $M_2$ represent the catalyst component, $n_1$ and $n_2$ represent the weight % of each catalyst component, and X represents a catalyst support.

Example 1: Deamination of Homoserine Lactone Hydrochloride Using Water as a Solvent

1) Example 1-1 (Primary Reaction)

As shown in FIG. 2, the deamination (primary reaction) of homoserine lactone hydrochloride performed using water as a solvent.

Specifically, 120 g of homoserine lactone hydrochloride (HSL.HCl), 70 g of water, and 10 mL of conc. HCl were added into a reactor and reacted while injecting NO/air ($O_2$) gas at 25° C. under atmospheric pressure (1 atm). After confirming the presence of unreacted HSL.HCl by GC analysis, the product was added into a separatory funnel and placed as it was until the layer separation was observed.

From the layer-separated solution, 31.67 g of the lower layer was recovered, and the solvent in the recovered lower layer was evaporated at 50° C. under reduced pressure (2 torr to 4 torr) to recover 28.96 g of the product. The analysis of the product revealed that the product contained 93.21% of chloro-gamma-butyrolactone (Cl-GBL), 3.85% of hydroxy-gamma-butyrolactone (HO-GBL), and 2.12% of furanone.

After separating the lower layer, 80 mL (92.24 g) from the upper layer (177.66 g) was used as a solvent for the secondary reaction. The remainder (85.42 g) was extracted three times with chloroform (70 mL/60 mL/60 mL), and the combined extracts were evaporated under reduced pressure to recover 22.36 g of the product. The analysis of the product components revealed that the product contained 91.70% of Cl-GBL, 3.08% of HO-GBL, and 4.52% of furanone.

After the chloroform extraction, the remainder (63.09 g) was evaporated under reduced pressure to recover 9.0 g of the product. The analysis of the product revealed that the product contained 2.47% of Cl-GBL, 95.78% of HO-GBL, and 0.59% of furanone.

2) Example 1-2 (Secondary Reaction)

As shown in FIG. 3, the deamination (secondary reaction) of HSL.HCl was performed using water as a solvent.

A part (80 mL; 92.24 g) of the upper layer recovered from the primary reaction and 120 g of HSL.HCl were added into a reactor and reacted while injecting NO/air ($O_2$) gas at 25° C. under atmospheric pressure (1 atm). After confirming the presence of unreacted HSL.HCl by GC analysis, the product was added into a separatory funnel and placed as it was until the layer separation was observed.

From the layer-separated solution, 64.04 g of the lower layer was recovered, and the solvent in the recovered lower layer was evaporated at 50° C. under reduced pressure (2 torr to 4 torr) to recover 58.28 g of the product. The analysis of the product revealed that the product contained 91.34% of Cl-GBL, 5.04% of HO-GBL, and 2.62% of furanone.

After separating the lower layer, 80 mL (94.25 g) from the upper layer (154.05 g) was used as a solvent for the tertiary reaction. The remainder (59.8 g) was extracted three times with chloroform (60 mL/60 mL/60 mL), and the combined extracts were evaporated under reduced pressure to recover 18.57 g of the product. The analysis of the product components revealed that the product contained 87.36% of Cl-GBL, 4.11% of HO-GBL, and 7.37% of furanone.

After the chloroform extraction, the remainder was evaporated under reduced pressure to recover 7.8 g of the product. The analysis of the product revealed that the product contained 2.28% of Cl-GBL, 91.44% of HO-GBL, and 0.92% of furanone.

3) Example 1-3 (Tertiary Reaction)

As shown in FIG. 4, the deamination (tertiary reaction) of HSL.HCl was performed using water as a solvent.

A part (80 mL; 94.25 g) of the upper layer recovered from the secondary reaction and 120 g of HSL.HCl were added into a reactor and reacted while injecting NO/air ($O_2$) gas at 25° C. under atmospheric pressure (1 atm). After confirming the presence of unreacted HSL.HCl by GC analysis, the product was added into a separatory funnel and placed as it was until the layer separation was observed.

From the layer-separated solution, 63.46 g of the lower layer was recovered, and the solvent in the recovered lower layer was evaporated at 50° C. under reduced pressure (2 torr to 4 torr) to recover 58.66 g of the product. The analysis of the product revealed that the product contained 91.80% of Cl-GBL, 4.84% of HO-GBL, and 2.36% of furanone.

After separating the lower layer, 80 mL (96.28 g) from the upper layer (154.05 g) was separated independently. The remainder (59.8 g) was extracted three times with chloroform (60 mL/60 mL/60 mL), and the combined extracts were evaporated under reduced pressure to recover 21.17 g of the product. The analysis of the product components revealed that the product contained 83.97% of Cl-GBL, 5.12% of HO-GBL, and 9.63% of furanone.

After the chloroform extraction, the remainder was evaporated under reduced pressure to recover 8.42 g of the product. The analysis of the product components revealed that the product contained 2.38% of Cl-GBL, 92.45% of HO-GBL, and 1.05% of furanone.

Example 2: Deamination of HSL.HCl Using Chloroform as a Solvent

Deamination of HSL.HCl was performed using a high pressure reaction system. Specifically, 2 g of HSL.HCl, 45 g of chloroform, and 1 g of conc. HCl were added into a container and reacted while injecting NO/air ($O_2$) gas at 25° C. under high pressure (about 14 atm). After reacting for 2 hours, the product was recovered and the product components were analyzed. The analysis revealed that the product contained 92.7% of Cl-GBL, 3.3% of HO-GBL, 3.8% of furanone, and 0.2% of other components.

Example 3: Deamination Reaction of Homoserine Lactone HSL.HCl Using Chloro-Gamma-Butyrolactone as a Solvent Cl-GBL (30 mL) was added as a solvent into a reactor and then HSL.HCl was sequentially added (10 g, 20 g, 30 g, 40 g, 50 g, 50 g, 50 g, 50 g, and 50 g) thereto, and reacted while injecting NO/air ($O_2$) gas at 25° C. under atmospheric pressure (1 atm). After confirming the presence of unreacted HSL.HCl by GC analysis, the product was added into a separatory funnel and placed as it was until the layer separation was observed.

The layer-separated product was separated into the upper layer and the lower layer in a volume ratio of about 1:4. The lower layer was recovered from the layer-separated solution and its components were analyzed. The analysis revealed that the lower layer contained 88.10% of Cl-GBL, 6.17% of HO-GBL, and 3.93% of furanone. The upper layer was recovered and the components were analyzed. The analysis revealed that the upper layer contained 71.11% of Cl-GBL, 20.07% of HO-GBL, and 6.02% of furanone.

Example 4: Deamination Reaction of Homoserine Lactone HSL.HCl Using a Catalyst

1) Example 4-1

Deamination of HSL.HCl was performed by adding to a reactor NO/$N_2$ and an aqueous solution of 10 wt % HSL.HCl under the supply conditions described below, using 2 g of each of Pt(5)/Ac and Pt(5)Au(5)/Ac as a catalyst.

Feed: 20 mL/min (NO/$N_2$=1/1, vol %), 0.03 mL/min (aqueous solution of 10 wt % HSL.HCl)

The reaction conditions were 60° C. and 20 atm, and a part of the product was recovered according to the reaction time and its components were analyzed. The results are shown in Table 1 below.

TABLE 1

| Catalyst | Reaction Time (Hr) | Conversion. (%) | Selectivity (%) | | |
|---|---|---|---|---|---|
| | | | Furanone | HO-GBL | Cl-GBL |
| Pt/Ac | 5 | 100 | 3.7 | 62.0 | 29.6 |
| | 25 | 94.3 | 9.0 | 32.9 | 48.6 |
| | 50 | 89.2 | 7.0 | 30.8 | 51.4 |
| | 75 | 69.0 | 6.9 | 27.3 | 47.0 |
| | 100 | 50.3 | 5.4 | 24.3 | 50.5 |
| PtAu/Ac | 5 | 100 | 5.6 | 35.2 | 55.3 |
| | 25 | 100 | 7.3 | 20.2 | 40.6 |
| | 50 | 100 | 6.6 | 19.2 | 41.9 |

Additionally, the above results are shown in graphs in FIG. 5.

2) Example 4-2

Deamination of HSL.HCl was performed by adding to a reactor NO/N$_2$ and an aqueous solution of 10 wt % HSL.HCl under the supply conditions described below, using 2.3 g of Fe$_2$O$_3$ as a catalyst.

Feed: 20 mL/min (NO/N$_2$=1/1 vol %+air (O$_2$)), 0.03 mL/min (aqueous solution of 10 wt % HSL.HCl)

The reaction was performed at the reaction temperature shown in Table 2 below at 20 atm, and a part of the product was recovered according to the reaction time and its components were analyzed. The results are shown in Table 2 below.

TABLE 2

| Reaction Temp (° C.) | Reaction Time (h) | Conv. (%) | Selectivity (%) | | |
|---|---|---|---|---|---|
| | | | Furanone | HO-GBL | Cl-GBL |
| 60 | 5 | 100 | 11.4 | 34.5 | 48.1 |
| 70 | 25 | 100 | 9.8 | 30.3 | 44.2 |
| 80 | 50 | 100 | 14.1 | 35.7 | 40.8 |
| 80 | 75 | 100 | 12.7 | 31.4 | 40.4 |
| 80 | 100 | 100 | 13.5 | 32.5 | 40.3 |
| 80 | 125 | 100 | 13.2 | 33.6 | 35.7 |
| 80 | 150 | 100 | 16.9 | 38.2 | 33.3 |

3) Example 4-3

Deamination of HSL.HCl was performed by adding to a reactor NO/N$_2$ and an aqueous solution of 10 wt % HSL.HBr under the supply conditions described below, using 2 g of Pt(5)/Ac as a catalyst.

Feed: 20 mL/min (NO/N$_2$=1/1, vol %), 0.03 mL/min (aqueous solution of 10 wt % HSL.HBr)

The reaction conditions were 60° C. and 20 atm, and a part of the product was recovered according to the reaction time and its components were analyzed. The results are shown in Table 3 below.

TABLE 3

| Reaction Temp (° C.) | Reaction Time (h) | Conv. (%) | Selectivity (%) | | |
|---|---|---|---|---|---|
| | | | Furanone | HO-GBL | Br-GBL |
| HSL•HBr | 5 | 100 | 5.9 | 50.7 | 35.5 |
| | 25 | 100 | 11.4 | 24.5 | 54.5 |
| | 50 | 100 | 10.7 | 25.4 | 48.8 |
| | 75 | 100 | 9.5 | 23.4 | 53.3 |
| | 100 | 100 | 9.5 | 26.4 | 54.0 |

4) Example 4-4

To a batch reactor were added as reactants 2 g each of HSL.HCl, homoserine (HS), and homoserine lactone free salt (HSL). 40 g of water and 0.1 g of Pt(5)/Ac were added to the reactor, and deamination of a homoserine-based compound was performed under the conditions described in Table 4 below. A part of the product was recovered according to the reaction time and its components were analyzed. The results are shown in Table 4 below.

TABLE 4

| Reactants | Reaction Pressure (atm) | | Reaction Temp (° C.) | Reaction Time (h) | Conv. (%) | Selectivity (%) | | |
|---|---|---|---|---|---|---|---|---|
| | NO/N$_2$ (50/50; v/v) | H$_2$ | | | | Furanone + GBL | HO-GBL | Cl-GBL |
| HSL•HBr | 15 | 0 | 60 | 3 | 100 | 19.6 | 21.2 | 36.9 |
| | 15 | 1.5 | 80 | 1 | 100 | 23.4 | 22.6 | 41.6 |
| | 15 | 1.5 | 80 | 3 | 100 | 26.5 | 20.5 | 42.3 |
| | 15 | 1.5 | 150 | 3 | 100 | 3.0 (GBL) | 72.5 | 3.8 |
| HS | 15 | 0 | 60 | 2 | 26.4 | 0 | 62.6 | 0 |
| | 15 | 0 | 80 | 2 | 36.8 | 0 | 63.5 | 0 |
| | 15 | 0 | 100 | 2 | 48.4 | 1.7 | 72.9 | 0 |
| | 15 | 0 | 120 | 2 | 61.5 | 1.2 | 76.5 | 0 |
| | 15 | 0 | 160 | 2 | 96.9 | 2.2 | 67.5 | 0 |
| HSL (free salt) | 15 | 0 | 60 | 2 | 3.0 | 0 | 46.5 | 0 |
| | 15 | 0 | 80 | 2 | 3.7 | 0 | 92.1 | 0 |
| | 15 | 0 | 100 | 2 | 6.2 | 0 | 86.2 | 0 |
| | 15 | 0 | 150 | 2 | 26.3 | 0 | 79.0 | 0 |

5) Example 4-5

Deamination of HSL.HCl was performed after adding the materials of i) to iii) below to a reactor:

i) 2 g of HSL.HCl, 0.1 g of Pt(5)/Ac, 40 g of water, and 15 atm of NO/N$_2$(1/1; v/v);

ii) 2 g of HSL.HCl, 0.1 g of Pt(5)/Ac, 40 g of water, 13.5 atm of N$_2$O/N$_2$(1/1; v/v), and 1 atm of O$_2$; or iii) 0.5 g of HSL.HCl, 6.5 g of water, HSL.HCl/HNO$_3$=1/1.5 m/m at 1 atm.

A part of the product was recovered according to the reaction time and its components were analyzed. The results are shown in FIG. 6 below.

6) Example 4-6

To a batch reactor were added as reactants 0.5 g of HSL.HCl and 6.5 g of water. Fe(NO$_3$)$_3$ was added to the reactor as a catalyst according to the ratio described in Table 5 below, and deamination of HSL.HCl was performed. The reaction conditions were 25° C. and 1 atm. A part of the product was recovered and its components were analyzed. The results are shown in Table 5 below.

TABLE 5

| Molar Ratio (Fe(NO$_3$)$_3$/ HSL•HCl) | Reaction Time (h) | Conv. (%) | Selectivity (%) | | |
|---|---|---|---|---|---|
| | | | Furanone | HO-GBL | Cl-GBL |
| 0.5 | 2 | 40.7 | 19.7 | 13.2 | 28.9 |
| 0.75 | 2 | 100 | 15.6 | 0 | 55.5 |
| 1.0 | 2 | 100 | 11.7 | 0 | 57 |
| 1.5 | 2 | 100 | 21.2 | 0 | 41.1 |

7) Example 4-7

To a reactor were added as reactants 0.5 g of HSL.HCl and 6.5 g of water. Fe(NO$_3$)$_3$ was added to the reactor as a catalyst in a molar ratio in which Fe(NO$_3$)$_3$/HSL.HCl was 0.5, and deamination of HSL.HCl was performed. The reaction temperature used is shown in Table 6 and the reaction pressure was 1 atm. A part of the product was recovered and its components were analyzed. The results are shown in Table 6 below.

TABLE 6

| Reaction Temp (° C.) | Reaction Time (h) | Conv. (%) | Selectivity (%) | | |
|---|---|---|---|---|---|
| | | | Furanone | HO-GBL | Cl-GBL |
| 25 (Ex. 4 to 6) | 2 | 40.7 | 19.7 | 13.2 | 28.9 |
| 60 | 2 | 100 | 21.5 | 0 | 46.6 |
| 80 | 2 | 100 | 17 | 0 | 41.4 |

8) Example 4-8

Deamination was performed in the same manner as in Example 4-6, except that the catalysts used were those shown in Table 7. A part of the product was recovered and its components were analyzed. The results are shown in Table 7 below.

TABLE 7

| Catalyst | Molar Ratio (Nitrite)Nitrate/ HSL•HCl | Reaction Time (h) | Conv. (%) | Selectivity (%) | | |
|---|---|---|---|---|---|---|
| | | | | Furanone | HO-GBL | Cl-GBL |
| NaNO$_2$ | 1/1 | 2 | 90.5 | 4.4 | 13.9 | 15.4 |
| Fe(NO$_3$)$_3$ | 0.75/1 | 2 | 100 | 15.6 | 0 | 55.5 |
| Al(NO$_3$)$_3$ | 0.75/1 | 3 | 100 | 30.3 | 1.4 | 42.4 |
| NH$_4$NO$_3$ | 2/1 | 8 | 100 | 14.5 | 15.1 | 35.1 |
| Cu(NO$_3$)$_3$ | 1.5/1 | 2 | 99.5 | 13.2 | 2.1 | 9.5 |
| Bi(NO$_3$)$_3$ | 1.5/1 | 2 | 100 | 19.2 | 1.4 | 9.6 |
| Zn(NO$_3$)$_2$ | 1.5/1 | 2 | 62.5 | 2.9 | 0 | 22.7 |

Additionally, the above results are shown in FIG. 7.

Example 5: Deamination of HSL.HCl Using Methanol as a Solvent

1) Example 5-1

To a reactor were added 1 g of HSL.HCl, 40 g of methanol, and 0.05 g of Pt(5)/Ac, and then NO/N$_2$ (15 atm, 1:1 (v/v)) was added. As described in Table 8, H$_2$ (6.5 atm) was further added to the reactor, and deamination of HSL.HCl was performed. A part of the product was recovered and its components were analyzed. The results are shown in Table 8 below.

TABLE 8

| Reaction Time (h) | | 2 | 2 | 2 | 2 | 5 |
|---|---|---|---|---|---|---|
| Reaction Temp (° C.) | | 60 | 80 | 100 | 120 | 120 |
| H$_2$ (atm) | | 0 | 0 | 0 | 6.5 | 6.5 |
| Conv. (%) | | 99.8 | 99.4 | 100 | 100 | 100 |
| Selectivity (%) | 4-Hydroxy-2-butenoic acid methyl ester | 0.6 | 6.1 | 7.9 | 8.5 | 9.2 |
| | Furanone/GBL | 2.9 | 13.4 | 19.0 | 10.8 | 18.3 |
| | HO-GBL | 0.1 | 0.3 | 0.3 | 1.6 | 0.1 |
| | MeO-GBL | 7.5 | 23.1 | 43.0 | 44.9 | 25.5 |
| | 4-Hydroxy-2-methoxybutanoic acid | 22.1 | 23.0 | 1.8 | 3.2 | 21.2 |
| | 4-Hydroxy-2-chlorobutanoic acid | 11.0 | 11.3 | 1.6 | 2.7 | 9.2 |
| | Cl-GBL | 4.1 | 10.9 | 16.1 | 15.5 | 6.5 |
| | Intermediates | 35.4 | 0.0 | 0.0 | 0.0 | 0.0 |
| | Others | 16.2 | 11.8 | 10.4 | 12.8 | 9.9 |

Additionally, the above results are shown in FIG. 8.

2) Example 5-2

To a reactor were added HSL.HCl, methanol, and/or water, as described in Table 9. To the reactor was added Pt(5)/Ac and then NO/N$_2$ (15 atm, 1:1 (v/v)). Deamination of HSL.HCl was performed at the reaction time and reaction temperature as described in Table 9. A part of the product was recovered and its components were analyzed, and the results are shown in Table 9 below.

TABLE 9

| | | | | | | |
|---|---|---|---|---|---|---|
| HSL·HCl (g) | | 1 | 2 | 2 | 2 | 2 |
| Pt(5)/Ac(g) | | 0.1 | 0.05 | 0.05 | 0.05 | 0.05 |
| Solvent | | MeOH (40 g) | MeOH (40 g) | MeOH:$H_2O$ = 3:1 (wt/wt) = 30 g:10 g | MeOH:$H_2O$ = 1:1 (wt/wt) = 20 g:20 g | $H_2O$ (40 g) |
| Reaction Temp (° C.) | | 100 | 100 | 100 | 100 | 60 |
| Reaction Time (h) | | 2 | 2 | 2 | 2 | 2 |
| Conv. (%) | | 100 | 92.8 | 100 | 100 | 99.8 |
| Selectivity (%) | 4-hydroxy-2-butenoic acid methyl ester | 7.9 | 6.0 | 3.8 | 1.3 | 0 |
| | Furanone | 19.0 | 18.2 | 8.1 | 8.6 | 19.6 |
| | HO-GBL | 0.3 | 0.3 | 8.6 | 21.4 | 21.2 |
| | MeO-GBL | 42.97 | 38.00 | 21.75 | 18.51 | 0 |
| | 4-Hydroxy-2-methoxybutanoic acid | 1.79 | 1.33 | 12.05 | 3.71 | 0 |
| | 4-Hydroxy-2-chlorobutanoic acid | 1.59 | 1.70 | 11.38 | 5.00 | 0 |
| | Cl-GBL | 16.1 | 22.9 | 13.1 | 13.8 | 36.9 |
| | Intermediates | 0.0 | 0.0 | 0.0 | 0.0 | 8.3 |
| | Others | 10.4 | 11.5 | 21.2 | 27.6 | 14.0 |

Additionally, the above results are shown in FIG. 9.

3) Example 5-3

To a reactor were added 1 g of HSL.HCl, 20 g of methanol, 20 g of chloroform, and 0.1 g Pt(5)/Ac. To the reactor was added $NO/N_2$ (15 atm, 1:1 (v/v)), and deamination of HSL.HCl was performed at the reaction time and reaction temperature as described in Table 10. A part of the product was recovered and its components were analyzed, and the results are shown in Table 10 below.

TABLE 10

| | | | | | |
|---|---|---|---|---|---|
| Reaction Temp (° C.) | | 60 | 60 | 80 | 80 |
| Reaction Time (h) | | 2 | 5 | 2 | 5 |
| Conv. (%) | | 98.9 | 100 | 100 | 100 |
| Selectivity (%) | 4-Hydroxy-2-butenoic acid methyl ester | 2 | 4.8 | 6.9 | 7.6 |
| | Furanone | 6.3 | 9 | 13.2 | 14.1 |
| | HO-GBL | 0.3 | 0.4 | 0.6 | 0.8 |
| | MeO-GBL | 20.2 | 17.3 | 25.4 | 24.b2 |

TABLE 10-continued

| | | | | |
|---|---|---|---|---|
| 4-Hydroxy-2-methoxybutanoic acid | 5.2 | 10.2 | 9 | 9.7 |
| 4-Hydroxy-2-chlorobutanoic acid | 8.5 | 14.6 | 13.2 | 12.7 |
| Cl-GBL | 26.1 | 14.7 | 22 | 20.1 |
| Intermediates | 21.1 | 21.2 | 0.4 | 0 |
| Others | 10.4 | 7.7 | 9.2 | 10.9 |

Additionally, the above results are shown in FIG. 10.

Example 6: Dechlorination of Chloro-Gamma-Butyrolactone

1) Example 6-1: Reactions Using Various Catalysts and Solvents

A reaction was performed after adding 3 g of each of Cl-GBL, the solvents of Table 11(30 g), and a catalyst to a reactor, and the degree of dechlorination of Cl-GBL was evaluated. The reaction was performed under atmospheric pressure (1 atm). A part of the product was recovered and its components were analyzed, and the results are shown in Table 11 below.

TABLE 11

| Catalyst | Amount of Catalyst Used (g) | Solvent | Temp (° C.) | Time (h) | Conv. (%) | Selectivity (%) | | | |
|---|---|---|---|---|---|---|---|---|---|
| | | | | | | 4-Chlorobutyric acid | GBL + Furanone | HO-GBL | Others |
| Pt(5)/Ac | 0.1 | GBL | 185 | 2 | 39.2 | 18.2 | 79.2 | 1.3 | 1.3 |
| Fresh Pd(5)/Ac | 0.1 | GBL | 160 | 4 | 96.6 | 9.7 | 88.7 | 0.7 | 0.9 |
| | 1.0 | GBL | 130 | 4 | 99.2 | 42.6 | 54.8 | 1.8 | 0.8 |
| | 1.0 | Diethylene glycol dimethylether | 130 | 4 | 93.4 | 0 | 96.3 | 2.6 | 1.1 |
| Used Pd(5)/Ac | 1.0 | DMSO | 140 | 4 | 97.9 | 0 | 48.5 | 42.4 | 9.2 |
| | 1.0 | Propylene carbonate | 130 | 4 | 93.3 | 0 | 94.1 | 3.5 | 2.4 |
| Rh(5)/Graphene Oxide | 0.1 | GBL | 160 | 4 | 97.1 | 19.7 | 76.6 | 1.3 | 2.4 |
| Rh(5)/Ac | 0.1 | GBL | 160 | 6 | 88.9 | 11.5 | 81.6 | 1.8 | 5.1 |

TABLE 11-continued

| Catalyst | Amount of Catalyst Used (g) | Solvent | Temp (° C.) | Time (h) | Conv. (%) | Selectivity (%) | | | |
|---|---|---|---|---|---|---|---|---|---|
| | | | | | | 4-Chlorobutyric acid | GBL + Furanone | HO-GBL | Others |
| Ni/Kiesel | 0.1 | GBL | 170 | 2 | 0 | — | — | — | — |
| Au/Ac | 0.1 | GBL | 170 | 2 | 0 | — | — | — | — |

2) Example 6-2: Reactions Using Pd/Ac as a Catalyst

Cl-GBL and $H_2$ were supplied to a reactor under the supply conditions described below, and Pd(5)/Ac was used as a catalyst.

Feed: $H_2$/Cl-GBL=43/1 m/m, WHSV=1.0 $h^{-1}$

The reaction conditions were 200° C. and atmospheric pressure (1 atm), and a part of the product was recovered according to the reaction time and its components were analyzed. The results are shown in Table 12 below.

TABLE 12

| Reaction Conditions | | | | | Selectivity (%) | | | | | GBL Yield (%) |
|---|---|---|---|---|---|---|---|---|---|---|
| Reaction Time (h) | Reaction Temp (° C.) | Gas Flow (mL/min) | $H_2$/Feed (m/m) | Conv. (%) | Butyric acid | 3-Chloropropanol | 4-Chlorobutyric acid | GBL | HO-GBL | |
| 65 | 200 | 180 | 43 | 100 | 0.75 | 0.03 | 0.32 | 97.83 | 0.76 | 97.83 |
| 99 | | | | 100 | 0.63 | 0.03 | 0.35 | 97.82 | 0.84 | 97.82 |
| 149 | | | | 100 | 0.52 | 0.03 | 0.32 | 97.97 | 0.85 | 97.98 |
| 210 | | | | 100 | 0.46 | 0.03 | 0.36 | 97.66 | 0.98 | 97.66 |
| 257 | | | | 100 | 0.39 | 0.03 | 0.27 | 97.93 | 0.94 | 97.93 |
| 307 | | | | 100 | 0.30 | 0.02 | 0.31 | 97.71 | 1.41 | 97.71 |
| 353 | | | | 100 | 0.26 | 0.06 | 0.34 | 97.75 | 1.50 | 97.81 |
| 410 | | | | 100 | 0.24 | 0.07 | 0.36 | 97.66 | 1.55 | 97.66 |
| 450 | | | | 100 | 0.22 | 0.06 | 0.39 | 97.64 | 1.59 | 97.64 |

3) Example 6-3: Reactions Using Pd/Ac as a Catalyst and 1,4-Dioxane as a Solvent $H_2$, Cl-GBL, and 1,4-dioxane were supplied to a reactor under the supply conditions described below, and Pd(5)/Ac was used as a catalyst.

Feed: 25/75 vol % Cl-GBL/1,4-dioxane, WHSV=1.5 $h^{-1}$

The reaction condition was atmospheric pressure (1 atm), and a part of the product produced was recovered and its components were analyzed. The results are shown in Table 13 below.

TABLE 13

| Reaction Conditions | | | | | Selectivity (%) | | | | | GBL + Furanone Yield (%) |
|---|---|---|---|---|---|---|---|---|---|---|
| Reaction Temp (° C.) | Gas Flow (mL/min) | $H_2$/Feed (m/m) | Reaction Time (h) | Conv. (%) | Butyric acid | 4-Chlorobutyric acid | GBL + Furanone | HO-GBL | Others | |
| 180 | 160 | 13.1 | 34 | 99.6 | 0.15 | 0.40 | 95.82 | 2.99 | 0.63 | 95.5 |
| 200 | 160 | 13.1 | 36 | 100 | 0.21 | 0.30 | 95.92 | 3.15 | 0.42 | 95.9 |
| 200 | 120 | 9.8 | 38 | 100 | 0.18 | 0.43 | 96.49 | 2.52 | 0.39 | 96.5 |
| 200 | 80 | 6.5 | 40 | 100 | 0.32 | 0.71 | 95.13 | 3.22 | 0.63 | 95.1 |

TABLE 13-continued

| | Reaction Conditions | | | | | Selectivity (%) | | | | GBL + |
|---|---|---|---|---|---|---|---|---|---|---|
| Reaction Temp (° C.) | Amount of Gas Flow (mL/min) | H₂/Feed (m/m) | Reaction Time (h) | Conv. (%) | Butyric acid | 4-Chlorobutyric acid | GBL + Furanone | HO-GBL | Others | Furanone Yield (%) |
| 200 | 60 | 4.9 | 43 | 100 | 0.19 | 0.35 | 97.69 | 1.41 | 0.36 | 97.7 |
| 200 | 40 | 3.3 | 46 | 99.6 | 0.44 | 1.38 | 94.23 | 2.95 | 1.00 | 93.9 |

4) Example 6-4: Reactions Using AuPd/Ac as a Catalyst and 1,4-dioxane as a Solvent Cl-GBL and 1,4-dioxane were supplied to a reactor under the supply conditions described below, and Au(5)Pd(5)/Ac was used as a catalyst.

Feed: 50/50 vol % Cl-GBL/1,4-dioxane, WHSV=1.0 h⁻¹

The reaction condition was atmospheric pressure (1 atm), and a part of the product was recovered according to the reaction time and its components were analyzed. The results are shown in Table 14 below.

TABLE 14

| | Reaction Conditions | | | | | Selectivity (%) | | | | GBL + |
|---|---|---|---|---|---|---|---|---|---|---|
| Reaction Time (h) | Reaction Temp (° C.) | Amount of Gas Flow (mL/min) | H₂/Feed (m/m) | Conv. (%) | Butyric acid | 4-Chlorobutyric acid | GBL + Furanone | HO-GBL | Others | Furanone Yield (%) |
| 2 | 200 | 120 | 30 | 100 | 0.00 | 0.12 | 96.99 | 2.68 | 0.21 | 97.0 |
| 4 | 200 | 120 | 30 | 100 | 0.25 | 0.14 | 97.15 | 2.29 | 0.18 | 97.2 |
| 6.5 | 200 | 120 | 30 | 100 | 0.25 | 0.24 | 95.87 | 3.22 | 0.42 | 95.9 |
| 9.5 | 200 | 120 | 30 | 100 | 0.28 | 0.24 | 95.87 | 3.19 | 0.41 | 95.9 |
| 12 | 220 | 120 | 30 | 100 | 0.48 | 0.17 | 95.84 | 3.08 | 0.43 | 95.8 |
| 15 | 240 | 120 | 30 | 100 | 0.84 | 0.15 | 95.42 | 2.76 | 0.83 | 95.4 |
| 18 | 260 | 120 | 30 | 100 | 1.35 | 0.16 | 95.48 | 2.29 | 0.71 | 95.5 |
| 20 | 260 | 120 | 30 | 100 | 2.29 | 0.17 | 94.86 | 1.73 | 0.95 | 94.9 |

5) Example 6-5: Reactions Using AuPd/Ac as a Catalyst without a Solvent

Cl-GBL and H₂ were supplied to a reactor under the supply conditions described below, and Au(5)Pd(5)/Ac was used as a catalyst.

Feed: H₂/Cl-GBL=38.5/1 m/m, WHSV=1.0 h⁻¹

The reaction condition was atmospheric pressure (1 atm), and a part of the product was recovered according to the reaction time and its components were analyzed. The results are shown in Table 15 below.

TABLE 15

| | Reaction Conditions | | | | | Selectivity (%) | | | | GBL |
|---|---|---|---|---|---|---|---|---|---|---|
| Reaction Time (h) | Reaction Temp (° C.) | Amount of Gas Flow (mL/min) | H₂/Feed (m/m) | Conv. (%) | Butyric acid | 3-Chloropropanol | 4-Chlorobutyric acid | GBL | HO-GBL | Yield (%) |
| 2 | 170 | 160 | 38.5/1 | 100 | 0.28 | 0.04 | 0.39 | 97.87 | 1.40 | 97.87 |
| 19 | | | | 100 | 0.19 | 0.04 | 0.56 | 97.43 | 1.63 | 97.43 |
| 20 | | | | 100 | 0.20 | 0.05 | 0.57 | 97.34 | 1.67 | 97.34 |
| 22 | | | | 100 | 0.19 | 0.05 | 0.55 | 97.37 | 1.65 | 97.37 |
| 32 | 200 | | | 100 | 0.55 | 0.04 | 0.36 | 97.34 | 1.57 | 97.34 |

TABLE 15-continued

| Reaction Time (h) | Reaction Temp (° C.) | Gas Flow (mL/min) | H₂/Feed (m/m) | Conv. (%) | Butyric acid | 3-Chloropropanol | 4-Chlorobutyric acid | GBL | HO-GBL | GBL Yield (%) |
|---|---|---|---|---|---|---|---|---|---|---|
| 48 | | | | 100 | 0.56 | 0.05 | 0.39 | 97.24 | 1.61 | 97.24 |
| 50 | | | | 100 | 0.56 | 0.05 | 0.40 | 97.18 | 1.62 | 97.18 |
| 54 | | | | 99.9 | 0.57 | 0.05 | 0.39 | 97.21 | 1.61 | 97.20 |

6) Example 6-6: Reactions Using Modified Pd/SiO₂ as a Catalyst and Dioxane as a Solvent Cl-GBL and dioxane were supplied to a reactor under the supply conditions described below, and a modified Pd(5)/SiO₂ was used as a catalyst.
Catalyst Composition: Pd(5)/PO₄(15)/SiO₂(Aerosil-380)
Supply Conditions: 50/50 vol % Cl-GBL/dioxane, WHSV=0.5 h⁻¹

The reaction conditions were the same as described in Table 16 below, and a part of the product was recovered according to the reaction time and its components were analyzed. The results are shown in Table 16 below.

TABLE 16

| Reaction Time (h) | Reaction Temp (° C.) | Amount of Gas Flow (mL/min) | H₂/Feed (m/m) | Conv. (%) | Butyric acid | 4-Chlorobutyric acid | GBL | Furanone | HO-GBL | GBL + Furanone Yield (%) |
|---|---|---|---|---|---|---|---|---|---|---|
| 11 | 250 | H₂ = 120 | 30 | 100 | 0.07 | 0.05 | 68.63 | 29.86 | 0.42 | 98.47 |
| 36 | 270 | | | 100 | 0.06 | 0.07 | 57.02 | 41.60 | 0.23 | 98.60 |
| 40 | 280 | | | 100 | 0.05 | 0.02 | 56.00 | 42.85 | 0.10 | 98.85 |
| 48 | 280 | H₂ = 60 N₂ = 60 | 15 | 100 | 0.03 | 0.07 | 49.81 | 48.53 | 0.35 | 98.32 |
| 50 | 280 | N₂ = 120 | 0 | 32.9 | 0.00 | 0.00 | 28.86 | 63.84 | 4.18 | 30.50 |

7) Example 6-7: Reactions Using Modified PdRe/SiO₂ as a Catalyst and Dioxane as a Solvent Cl-GBL and dioxane were supplied to a reactor under the supply conditions described below, and a modified Pd(5)Re(5)/SiO₂ was used as a catalyst.
Catalyst Composition: Pd(5)Re(5)/PO₄(15)/SiO2 (Aerosil-380)
Supply Conditions: 50/50 vol % Cl-GBL/dioxane, WHSV=1.0 h⁻¹

The reaction conditions were the same as described in Table 17 below, and a part of the product was recovered according to the reaction time and its components were analyzed. The results are shown in Table 17 below.

TABLE 17

| Reaction Time (h) | Reaction Temp (° C.) | Amount of Gas Flow (mL/min) | H₂/Feed (m/m) | Conv. (%) | Butyric acid | 4-Chlorobutyric acid | GBL | Furanone | HO-GBL | GBL + Furanone Yield (%) |
|---|---|---|---|---|---|---|---|---|---|---|
| 14 | 250 | H₂ = 120 | 30 | 100.0 | 0.45 | 0.04 | 75.53 | 22.35 | 0.42 | 97.88 |
| 26 | | | | 100.0 | 0.41 | 0.11 | 67.81 | 29.74 | 0.69 | 97.55 |
| 32 | | | | 100.0 | 0.80 | 0.13 | 60.07 | 35.75 | 1.06 | 95.81 |

8) Example 6-8: Reactions Using Modified Rh/SiO$_2$ as a Catalyst and Dioxane as a Solvent Cl-GBL and dioxane were supplied to a reactor under the supply conditions described below, and a modified Rh(5)/SiO$_2$ was used as a catalyst.

Catalyst Composition: Rh(5)/PO$_4$(15)/SiO$_2$ (Aerosil-380)
Supply Conditions: 50/50 vol % Cl-GBL/dioxane, WHSV=1.0 h$^{-1}$ The reaction conditions were the same as described in Table 18 below, and a part of the product was recovered according to the reaction time and its components were analyzed. The results are shown in Table 18 below.

TABLE 18

| Reaction Conditions | | | | | Selectivity (%) | | | | | GBL + |
|---|---|---|---|---|---|---|---|---|---|---|
| Reaction Time (h) | Reaction Temp (° C.) | Amount of Gas Flow (mL/min) | H$_2$/ Feed (m/m) | Conv. (%) | Butyric acid | 4-Chlorobutyric acid | GBL | Furanone | HO-GBL | Furanone Yield (%) |
| 10 | 250 | H$_2$ = 120 | 30 | 99.9 | 5.29 | 0.09 | 85.96 | 5.12 | 0.87 | 91.01 |
| 25 | | | | 99.9 | 1.13 | 0.09 | 54.96 | 39.07 | 1.69 | 93.89 |

9) Example 6-9: Reactions Using Rh(5)/Ac as a Catalyst and Dioxane as a Solvent

Cl-GBL and dioxane were supplied to a reactor under the supply conditions described below, and a modified Rh(5)/Ac was used as a catalyst.

Supply Conditions: 50/50 vol % Cl-GBL/dioxane, WHSV=1.0 h$^{-1}$

The reaction conditions were the same as described in Table 19 below, and a part of the product was recovered according to the reaction time and its components were analyzed. The results are shown in Table 19 below.

TABLE 19

| Reaction Conditions | | | | | Selectivity (%) | | | | | GBL |
|---|---|---|---|---|---|---|---|---|---|---|
| Reaction Time (h) | Reaction Temp (° C.) | WHSV (h$^{-1}$) | H$_2$/ Feed (m/m) | Conv. (%) | Butyric acid | 3-Chloropropanol | 4-Chlorobutyric acid | GBL | Hydroxy-GBL | Yield (%) |
| 2 | 250 | 1.0 | 30 | 100 | 12.95 | — | 0.18 | 85.51 | 0.59 | 85.51 |
| 4 | 230 | | | 100 | 6.95 | — | 0.12 | 90.87 | 1.51 | 90.87 |
| 7 | 215 | | | 100 | 4.49 | — | 0.17 | 92.96 | 1.92 | 92.96 |
| 11 | 200 | | | 100 | 3.77 | — | 0.22 | 93.69 | 1.95 | 93.69 |
| 14 | 190 | | | 100 | 2.72 | — | 0.17 | 94.47 | 2.36 | 94.47 |
| 17 | 180 | | | 100 | 2.16 | — | 0.37 | 94.03 | 3.08 | 94.03 |

10) Example 6-10: Reactions Using Pd(4.5)Pt(0.5)/Ac as a Catalyst

Cl-GBL was supplied to a reactor under the supply conditions described in Table 20 below and Pd(4.5)Pt(0.5)/Ac was used as a catalyst.

The reaction conditions were the same as described in Table 20 below, and a part of the product was recovered according to the reaction time and its components were analyzed. The results are shown in Table 20 below.

TABLE 20

| Supply | Reaction Time (h) | Reaction Temp (° C.) | WHSV (h⁻¹) | H₂/Feed (m/m) | Conv. (%) | Butyric acid | 3-Chloropropanol | 4-Chlorobutyric acid | GBL | Hydroxy-GBL | GBL Yield (%) |
|---|---|---|---|---|---|---|---|---|---|---|---|
| Cl-GBL | 10 | 200 | 1.0 | 43 | 100 | 1.51 | 0.02 | 0.29 | 97.89 | 0.25 | 97.89 |
|  | 57 | 200 |  | 43 | 100 | 1.31 | 0.04 | 0.37 | 97.87 | 0.37 | 97.87 |
|  | 65 | 150 |  | 22 | 99.99 | 0.48 | 0.03 | 1.90 | 97.14 | 0.01 | 97.14 |
|  | 81 | 150 |  | 11 | 99.94 | 0.46 | 0.04 | 1.78 | 97.15 | 0.42 | 97.09 |
|  | 87 | 150 |  | 11 | 82.67 | 0.73 | 0.05 | 3.05 | 95.26 | 0.33 | 78.76 |
| Cl-GBL | 11 | 200 | 1.0 | 43 | 100 | 1.73 | 0.03 | 0.31 | 97.57 | 0.30 | 97.57 |
|  | 53 |  |  |  | 100 | 1.43 | 0.03 | 0.27 | 97.80 | 0.43 | 97.80 |
|  | 101 |  |  |  | 100 | 1.44 | 0.03 | 0.34 | 97.49 | 0.57 | 97.49 |
|  | 149 |  |  |  | 100 | 1.26 | 0.12 | 0.35 | 97.66 | 0.55 | 97.66 |
|  | 166 |  |  |  | 99.99 | 0.99 | 0.23 | 0.35 | 97.79 | 0.54 | 97.78 |

11) Example 6-11: Reactions Using PdM/Ac as a Catalyst

Cl-GBL was supplied to a reactor using the catalysts and supply conditions described in Table 21 below. The reaction conditions were the same as described in Table 21 below, and a part of the product was recovered according to the reaction time and its components were analyzed. The results are shown in Table 21 below.

TABLE 21

| Catalyst | Reaction Time (h) | Reaction Temp (° C.) | WHSV (h⁻¹) | H₂/Feed (m/m) | Conv. (%) | Butyric acid | 3-Chloropropanol | 4-Chlorobutyric acid | GBL | Hydroxy-GBL | GBL Yield (%) |
|---|---|---|---|---|---|---|---|---|---|---|---|
| Pd(5) | 3 | 200 | 1.0 | 43 | 100 | 0.42 | 0.03 | 0.36 | 98.16 | 0.95 | 98.16 |
| Re (5)/Ac | 27 |  |  |  | 100 | 0.25 | 0.04 | 0.36 | 97.72 | 1.48 | 97.72 |
|  | 50 |  |  |  | 100 | 0.22 | 0.05 | 0.35 | 97.71 | 1.56 | 97.71 |
| Pd(5) Ni (1.25)/ Ac | 24 |  |  |  | 100 | 0.65 | 0.05 | 0.37 | 98.24 | 0.492 | 98.24 |
|  | 56 |  |  |  | 100 | 0.54 | 0.05 | 0.396 | 98.35 | 0.569 | 98.35 |
|  | 94 |  |  |  | 99.99 | 0.44 | 0.05 | 0.357 | 97.88 | 1.165 | 97.88 |
| Pd(5) Fe (1.25)/ Ac | 3 |  |  |  | 100 | 3.35 | 0.02 | 0.29 | 96.16 | 0.05 | 96.16 |
|  | 8 |  |  |  | 100 | 2.14 | 0.02 | 0.32 | 97.16 | 0.27 | 97.16 |
|  | 32 |  |  |  | 99.99 | 0.46 | 0.06 | 0.33 | 98.60 | 0.44 | 98.59 |

12) Example 6-12: Reactions Using PdM/Support as a Catalyst

Cl-GBL was supplied to a reactor using the catalysts and supply conditions described in Table 22 below. The reaction conditions were the same as described in Table 22 below, and a part of the product was recovered according to the reaction time and its components were analyzed. The results are shown in Table 22 below.

TABLE 22

| Catalyst | Reaction Time (h) | Reaction Temp (° C.) | WHSV (h⁻¹) | H₂/Feed (m/m) | Conv. (%) | Butyric acid | 3-Chloropropanol | 4-Chlorobutyric acid | GBL | Hydroxy-GBL | GBL Yield (%) |
|---|---|---|---|---|---|---|---|---|---|---|---|
| Pd(5) | 5 | 200 | 1.0 | 43 | 100 | 16.10 | 0.06 | 0.14 | 83.58 | 0.03 | 83.58 |
| Pt(0.55)/ (97) ZrO₂-(3)Al₂O₃ | 27 |  |  |  | 100 | 3.36 | 0.03 | 0.25 | 96.08 | 0.18 | 96.10 |
|  | 34 |  |  |  | 99.99 | 2.87 | 0.03 | 0.27 | 96.44 | 0.26 | 96.43 |
|  | 60 |  |  |  | 99.95 | 1.78 | 0.04 | 0.31 | 97.41 | 0.36 | 97.40 |
| Pd/TiO₂ | 2 |  |  |  | 99.75 | 2.10 | 0.05 | 0.21 | 97.35 | 0.13 | 97.11 |

TABLE 22-continued

| Catalyst | Reaction Conditions | | | | | Selectivity (%) | | | | | |
|---|---|---|---|---|---|---|---|---|---|---|---|
| | Reaction Time (h) | Reaction Temp (°C.) | WHSV (h⁻¹) | $H_2$/Feed (m/m) | Conv. (%) | Butyric acid | 3-Chloropropanol | 4-Chlorobutyric acid | GBL | Hydroxy-GBL | GBL Yield (%) |
| (P-25) (Sintering at 650° C.) | 4 | | | | 99.44 | 1.52 | 0.06 | 0.21 | 97.89 | 0.24 | 97.34 |
| Pd(5)/ Aerosil-380 (Unsintered) | 25 | | | | 100 | 0.21 | 0.02 | 0.10 | 98.85 | 0.73 | 98.85 |
| | 50 | | | | 100 | 0.15 | 0.04 | 0.12 | 98.37 | 1.19 | 98.37 |
| | 105 | | | | 99.99 | 0.16 | 0.05 | 0.11 | 99.12 | 0.45 | 99.12 |
| | 125 | | | | 99.96 | 0.13 | 0.06 | 0.15 | 99.02 | 0.53 | 98.99 |
| Pd(5)/ Aerosil-380 (Sintering at 650° C.) | 25 | | | | 100 | 0.31 | 0.04 | 0.12 | 99.17 | 0.31 | 99.17 |
| | 50 | | | | 100 | 0.25 | 0.04 | 0.14 | 99.07 | 0.43 | 99.07 |
| | 151 | | | | 100 | 0.22 | 0.05 | 0.23 | 98.23 | 1.18 | 98.23 |
| | 202 | | | | 100 | 0.19 | 0.05 | 0.22 | 98.08 | 1.34 | 98.08 |
| | 250 | | | | 100 | 0.19 | 0.05 | 0.25 | 97.75 | 1.63 | 97.75 |
| | 320 | | | | 100 | 0.18 | 0.05 | 0.26 | 97.71 | 1.67 | 97.71 |

Example 7: Hydrogenationdehydration of Hydroxy-Gamma-Butyrolactone

1) Example 7-1: Reactions Using Various Catalysts

The hydrogenation-dehydration of HO-GBL was performed as follows. Specifically, to a reactor were supplied HO-GBL and 1,4-dioxane under the supply conditions described below, and Pd(5)/Ac, Re(5)/Ac, Pd(5)Te(3.3)/Ac, Pd(5)Re(5)/Ac, Pt(5)Re(5)/Ac, and Rh(5)Re(5)/Ac were used as catalysts.

Feed: 25/75 v/v HO-GBL/dioxane, $H_2$/HO-GBL=110/1 m/m, WHSV=0.15 $h^{-1}$

The reaction conditions were 250° C. and 5 atm, and a part of the product was recovered according to the reaction time and its components were analyzed. The results are shown in Table 23 below.

TABLE 23

| Catalyst | Reaction Time (h) | Conv. (%) | Selectivity (%) | | | | | | | | |
|---|---|---|---|---|---|---|---|---|---|---|---|
| | | | THF | 2-PrOH | 2-BuOH | 1-PrOH | 1-BuOH | 2-HO-THF | GBL | Butyric acid | Others |
| Pd/Ac | 4 | 98.75 | 0.2 | 1.0 | 2.8 | 0.1 | 0.1 | 0.1 | 17.6 | 64.0 | 14.2 |
| | 10 | 95.17 | 0.1 | 0.5 | 1.6 | 0.0 | 0.1 | 0.1 | 17.0 | 51.5 | 29.0 |
| Re/Ac | 6 | 99.96 | 1.8 | 2.3 | 1.6 | 2.9 | 7.6 | 0.9 | 76.8 | 2.1 | 3.9 |
| | 10 | 90.46 | 1.0 | 2.5 | 0.6 | 2.9 | 3.7 | 1.2 | 75.3 | 5.7 | 7.1 |
| | 25.5 | 60.88 | 1.9 | 0.1 | 0.1 | 2.1 | 0.2 | 1.1 | 68.2 | 7.4 | 18.7 |
| PdTe/Ac | 3.5 | 56.35 | 0.2 | 0.5 | 2.3 | 0.6 | 0.5 | 0.2 | 43.0 | 34.6 | 18.2 |
| | 5 | 48.19 | 0.2 | 0.4 | 1.5 | 0.5 | 0.5 | 0.1 | 35.3 | 38.9 | 22.7 |
| PdRe/Ac | 5 | 99.85 | 26.2 | 2.7 | 2.3 | 8.4 | 12.4 | 1.1 | 43.2 | 0.5 | 3.1 |
| | 11.5 | 99.99 | 9.7 | 2.0 | 2.5 | 8.5 | 13.8 | 2.0 | 55.0 | 1.4 | 5.0 |
| | 25 | 99.78 | 4.0 | 2.1 | 1.8 | 9.0 | 9.9 | 2.8 | 58.4 | 6.4 | 5.5 |
| PtRe/Ac | 5.5 | 99.89 | 18.4 | 4.4 | 4.0 | 9.3 | 20.0 | 1.5 | 39.7 | 0.0 | 2.8 |
| | 10 | 99.99 | 6.5 | 3.2 | 3.6 | 9.0 | 18.0 | 2.7 | 52.2 | 0.0 | 4.8 |
| | 14.5 | 99.98 | 4.1 | 3.1 | 3.4 | 9.4 | 17.1 | 3.3 | 53.7 | 1.0 | 4.9 |
| RhRe/Ac | 5 | 99.72 | 29.4 | 2.3 | 2.4 | 5.1 | 4.2 | 0.5 | 53.2 | 0.6 | 2.4 |
| | 11 | 99.88 | 16.5 | 1.9 | 3.2 | 5.9 | 5.9 | 1.0 | 63.0 | 0.7 | 1.9 |
| | 26.5 | 99.92 | 5.5 | 2.8 | 2.6 | 5.1 | 6.4 | 1.6 | 69.0 | 2.2 | 4.9 |
| | 54.5 | 99.90 | 3.7 | 2.7 | 2.0 | 4.5 | 5.7 | 1.9 | 69.7 | 4.7 | 5.2 |
| | 57 | 99.90 | 3.4 | 2.7 | 1.9 | 4.3 | 5.5 | 1.8 | 69.5 | 4.8 | 6.0 |

2) Example 7-2: Reactions Using RhRe/Ac as a Catalyst

Reactions were performed in the same manner as in Example 7-1, except that Rh(2.5)Re(5)/Ac was used as a catalyst. The results are shown in Table 24.

TABLE 24

| Reaction Time (h) | Conv. (%) | Selectivity (%) | | | | | | | | |
|---|---|---|---|---|---|---|---|---|---|---|
| | | THF | 2-PrOH | 2-BuOH | 1-PrOH | 1-BuOH | 2-HO-THF | GBL | Butyric acid | Others |
| 5 | 99.9 | 12.8 | 2.5 | 2.9 | 4.6 | 6.2 | 1.2 | 67.1 | 0.4 | 2.4 |
| 10.5 | 99.8 | 5.0 | 2.3 | 2.7 | 4.4 | 6.4 | 1.8 | 72.5 | 1.7 | 3.2 |
| 24.5 | 97.3 | 1.6 | 2.6 | 1.3 | 4.2 | 4.2 | 2.2 | 72.4 | 5.0 | 6.4 |
| 31 | 95.2 | 1.5 | 2.7 | 1.0 | 4.4 | 3.5 | 2.5 | 69.1 | 6.3 | 9.1 |
| 37 | 93.9 | 0.2 | 4.6 | 0.9 | 4.8 | 3.4 | 2.5 | 70.0 | 6.4 | 7.3 |
| 38 | 92.8 | 1.9 | 2.8 | 0.9 | 4.6 | 3.1 | 2.5 | 69.1 | 6.9 | 8.2 |

3) Example 7-3: Reactions Using RhRe/SiO$_2$ as a Catalyst

Reactions were performed in the same manner as in Example 7-1, except that Rh(5)Re(5)/SiO$_2$ was used as a catalyst. The results are shown in Table 25.

TABLE 25

| Reaction Time (h) | Conv. (%) | Selectivity (%) | | | | | | | | |
|---|---|---|---|---|---|---|---|---|---|---|
| | | THF | 2-PrOH | 2-BuOH | 1-PrOH | 1-BuOH | 2-HO-THF | GBL | Butyric acid | Others |
| 5 | 99.9 | 1.4 | 0.0 | 5.8 | 3.1 | 7.7 | 0.0 | 53.3 | 9.6 | 19.1 |
| 9.5 | 99.0 | 0.7 | 0.0 | 4.1 | 5.2 | 3.7 | 0.0 | 51.0 | 24.9 | 10.4 |
| 26 | 99.8 | 0.2 | 0.0 | 2.6 | 8.1 | 2.0 | 0.0 | 51.8 | 28.4 | 7.0 |
| 29 | 97.5 | 0.2 | 0.0 | 2.2 | 8.6 | 1.8 | 0.0 | 47.6 | 31.8 | 7.9 |

4) Example 7-4: Reactions with Changes in Reaction Pressure

Reactions were performed in the same manner as in Example 7-1, except that Rh(5)Re(5)/Ac was used as a catalyst and the reaction temperature and reaction pressure were changed as shown in Table 26, and the reactions were performed for 90 hours. The results are shown in Table 26.

TABLE 26

| Reaction Temp (° C.) | Reaction Pressure (atm) | Conv. (%) | Selectivity (%) | | | | | | | | |
|---|---|---|---|---|---|---|---|---|---|---|---|
| | | | THF | 2-PrOH | 2-BuOH | 1-PrOH | 1-BuOH | 2-HO-THF | GBL | Butyric acid | Others |
| 240 | 5 | 96.95 | 2.8 | 3.1 | 1.8 | 4.5 | 6.0 | 2.6 | 69.1 | 4.2 | 6.1 |
| 250 | 1 | 81.37 | 0.9 | 0.9 | 0.1 | 0.9 | 0.4 | 1.1 | 75.8 | 12.3 | 7.6 |
| 250 | 5 | 99.90 | 3.4 | 2.7 | 1.9 | 4.3 | 5.5 | 1.8 | 69.5 | 4.8 | 6.0 |
| 250 | 15 | 100.0 | 14.0 | 3.5 | 5.6 | 8.5 | 15.1 | 4.5 | 41.6 | 0.6 | 6.7 |
| 250 | 25 | 100.0 | 21.6 | 3.3 | 6.9 | 9.7 | 19.2 | 6.9 | 23.3 | 0.4 | 8.6 |
| 250 | 35 | 100.0 | 25.6 | 2.9 | 7.3 | 9.8 | 21.1 | 8.9 | 14.8 | 0.4 | 9.3 |

5) Example 7-5: Reactions Using RhRe/SiO$_2$ as a Catalyst

HO-GBL and 1,4-dioxane were supplied to a reactor under the supply conditions described below and 2 g of Rh(5)Re(5)/SiO$_2$ (HI-SIL233) was used as a catalyst.

Feed: 50/50 vol % HO-GBL/1,4-Dioxane, H$_2$/HO-GBL=50/1, WHSV: 0.3 h$^{-1}$

The reaction conditions were 250° C. and 5 atm, and a part of the product was recovered according to the reaction time and its components were analyzed. The results are shown in Table 27 below.

TABLE 27

| Reaction Time (h) | Conv. (%) | Selectivity (%) | | | | | | |
|---|---|---|---|---|---|---|---|---|
| | | 1-PrOH | 2-BuOH | 1-BuOH | THF | Butyric acid | 1,3-PDO | GBL |
| 4 | 99.5 | 3.6 | 5.1 | 2.9 | 3.6 | 1.1 | 1.2 | 78.0 |
| 7 | 99.9 | 5.3 | 5.9 | 2.4 | 3.3 | 2.4 | 1.5 | 75.0 |
| 15 | 90.7 | 5.7 | 5.7 | 1.4 | 6.2 | 7.9 | 1.5 | 67.8 |
| 25 | 46.6 | 4.9 | 6.0 | 0.5 | 5.4 | 16.1 | 2.5 | 51.3 |

Example 8: Acetylation and Deacetylation of Hydroxy-Gamma-Butyrolactone

Acetylation and deacetylation of HO-GBL were performed as follows.

1) Example 8-1

At room temperature under atmospheric pressure, 10 g of acetyl chloride was added to 5 g of HO-GBL while stirring. In particular, HCl gas was produced in the form of fumes by acetylation and heat was generated. After stirring for 30 minutes at room temperature, the reaction was stopped, and the reaction product was analyzed. The analysis revealed that the conversion of hydroxy-gamma-butyrolactone was 99.97%, and the yield of acetoxy-gamma-butyrolactone produced therein was 93.24%.

2) Example 8-2

A HO-GBL-containing sample (108 g) containing HO-GBL (92.22 wt %), Cl-GBL (2.67 wt %), and furanone (1.83 wt %) was added into a reactor, and then acetic anhydride (117 g) was added, and refluxed under heat at 135° C. Upon completion of the reaction, the resultant was subjected to distillation under reduced pressure (80° C., about 3 torr) to obtain 143 g of a product, and the product components were analyzed. The analysis revealed that the product contained acetoxy-gamma-butyrolactone (acetoxy-GBL; 87.83 wt %), Cl-GBL (1.68 wt %), and furanone (0.95 wt %).

The above product was again subjected to distillation under reduced pressure (135° C. to 145° C., about 5 torr) to obtain a product containing acetoxy-GBL (92.35 wt %), Cl-GBL (4.31 wt %), and furanone (1.19 wt %).

The above product was subjected to deacetoxylation under the reaction conditions shown in Table 28, and the results are shown in Table 28.

TABLE 28

| Supply Rate (mL/min) | Reaction Pressure (atm) | Reaction Temp (° C.) | Amount of Gas Flow (mL/min) | Conv. (%) | Selectivity (%) | | | | |
|---|---|---|---|---|---|---|---|---|---|
| | | | | | Acrolein | Butyl Acetate | Furanone | Cl-GBL | Others |
| 0.02 | 1 | 475 | 35(N$_2$) | 48.1 | 0.1 | 0.67 | 88.26 | 2.74 | 5.28 |
| 0.02 | 1 | 475 | 35(N$_2$) | 48.0 | 0 | 0.72 | 88.50 | 2.99 | 5.00 |
| 0.02 | 1 | 500 | 35(N$_2$) | 78.4 | 2.73 | 1.93 | 85.05 | 1.61 | 5.76 |
| 0.02 | 1 | 500 | 35(N$_2$) | 78.5 | 2.27 | 2.05 | 85.91 | 0.98 | 6.00 |
| 0.015 | 1 | 500 | 35(N$_2$) | 77.7 | 1.63 | 1.53 | 87.50 | 0.79 | 5.58 |
| 0.015 | 1 | 500 | 35(N$_2$) | 78.2 | 1.29 | 1.57 | 88.10 | 0.80 | 5.33 |
| 0.02 | 1 | 500 | 35(N$_2$) | 97.7 | 38.35 | 3.45 | 45.70 | 1.93 | 11.39 |

Example 9: Dehydration Reaction of Hydroxy-Gamma-Butyrolactone

The hydrogenation-dehydration at the time of conversion from HO-GBL to GBL was performed using the catalysts (amount of catalyst used: 2 g) and the conditions (feed rate: 0.02 mL/min; reaction pressure: atmospheric pressure) shown in Table 29.

TABLE 29

| Catalyst | Feed | Reaction Temp (° C.) | Amount of Gas Flow (mL/min) | WHSV (h$^{-1}$) | Reaction Time (h) | Conv. | Selectivity (%) | | | Yield (%) |
|---|---|---|---|---|---|---|---|---|---|---|
| | | | | | | | Acrolein | Furanone | Others | Furanone |
| Sintering at 600 Hydroxy-apatite (HAP) | Cl-GBL (50)/ 1,4-Dioxane (50) vol % | 280 | 80(N$_2$) | 0.300 | 2 | 3.0 | 10.59 | 22.64 | 66.78 | 0.7 |
| | | 350 | 80(N$_2$) | 0.300 | 6 | 26.0 | 19.18 | 9.64 | 71.17 | 2.5 |

TABLE 29-continued

| Catalyst | Feed | Reaction Temp (° C.) | Amount of Gas Flow (mL/min) | WHSV (h⁻¹) | Reaction Time (h) | Conv. | Selectivity (%) | | | Yield (%) Furanone |
|---|---|---|---|---|---|---|---|---|---|---|
| | | | | | | | Acrolein | Furanone | Others | |
| 50 wt InPO₄/ TiO₂ (In/P = 1/1.7 m/m) | | 280 | 50(H₂) | 0.300 | 2 | 2.6 | 7.27 | 60.21 | 32.52 | 1.5 |
| | | 320 | 50(H₂) | 0.300 | 5 | 7.7 | 3.10 | 72.07 | 24.83 | 5.5 |
| | | 350 | 30(H₂) | 0.300 | 8 | 18.7 | 14.08 | 60.81 | 25.12 | 11.3 |
| 50 wt FePO₄/ alpha- Al₂O₃ (In/Fe = 1/1 m/m) | | 300 | 30(H₂) | 0.300 | 2 | 3.2 | 7.61 | 38.54 | 53.85 | 1.2 |
| | | 330 | 30(H₂) | 0.300 | 5 | 6.6 | 6.16 | 57.32 | 36.53 | 3.8 |
| | | 350 | 30(H₂) | 0.300 | 12 | 7.4 | 7.38 | 55.93 | 36.69 | 4.1 |
| | | 350 | 30(H₂) | 0.300 | 14 | 6.7 | 6.86 | 50.23 | 42.91 | 3.4 |
| 16 wt WO₃/ ZrO₂ | | 280 | 60(N₂) | 0.300 | 2 | 27.0 | 29.90 | 37.24 | 32.86 | 10.1 |
| | | 280 | 60(N₂) | 0.300 | 5 | 17.3 | 18.58 | 42.06 | 39.37 | 7.3 |
| Sintering at 300 15 wt H₃PW₁₂/SiO₂ | | 280 | 60(N₂) | 0.300 | 4 | 10.1 | 14.48 | 44.32 | 41.20 | 4.5 |
| 15 wt PO₄/SiO₂ | | 300 | 30(N₂) | 0.300 | 2 | 96.6 | 65.52 | 19.53 | 14.95 | 18.9 |
| | | 300 | 30(N₂) | 0.300 | 3 | 98.9 | 35.10 | 51.94 | 12.96 | 51.4 |
| | | 280 | 60(N₂) | 0.300 | 6 | 59.2 | 14.03 | 71.96 | 14.01 | 42.6 |
| | | 280 | 60(N₂) | 0.300 | 12 | 56.7 | 11.00 | 73.10 | 15.99 | 41.5 |
| 30 wt PO₄/SiO₂ | | 280 | 60(N₂) | 0.300 | 2 | 81.5 | 55.20 | 31.54 | 13.25 | 25.7 |
| | | 280 | 60(N₂) | 0.300 | 3 | 46.9 | 17.26 | 64.21 | 18.52 | 30.1 |
| | | 280 | 60(N₂) | 0.300 | 4 | 34.0 | 11.26 | 67.79 | 20.95 | 23.0 |
| | | 280 | 60(H₂) | 0.300 | 8 | 25.5 | 2.89 | 64.85 | 32.26 | 16.5 |
| 15 wt PO₄/TiO₂ | | 280 | 30(N₂) | 0.300 | 3 | 73.2 | 25.75 | 37.84 | 36.41 | 27.69 |
| | | 280 | 30(N₂) | 0.300 | 5 | 84.8 | 9.14 | 17.93 | 72.93 | 15.21 |

Example 10: Hydrogenation of Gamma-Butyrolactone

1) Example 10-1

1,4-Butanediol (1,4-BDO) was prepared from GBL by hydrogenation. Specifically, H₂ and GBL were supplied to a reactor under the conditions shown in Table 30 below, and CuO(72.2)MnO₂(2.5)ZnO(0.3)SiO₂(25) (the values within the parentheses represent wt %), which was prepared as described in Example 1 of Korean Patent No. 10-0538979, was used as a catalyst. The product components were analyzed and the results are shown in Table 30 below.

TABLE 30

| Reaction Temp (° C.) | Reaction Pressure (atm) | Reaction Time (h) | H₂/GBL (m/m) | Conv. (%) | Selectivity (%) | |
|---|---|---|---|---|---|---|
| | | | | | 1,4-BDO | THF |
| 180 | 30 | 7 | 26 | 83.3 | 98.1 | 0.7 |
| | 35 | 25 | 26 | 89.5 | 98.4 | 0.8 |
| | 40 | 52 | 26 | 92.0 | 98.3 | 1.0 |
| | 40 | 55 | 27.5 | 91.8 | 98.4 | 0.9 |
| 185 | 40 | 70 | 26.0 | 86.7 | 97.7 | 1.5 |
| 177 | 40 | 85 | 26.0 | 92.8 | 98.7 | 0.8 |
| 175 | 40 | 109 | 29.2 | 94.2 | 98.3 | 0.9 |
| 172 | 40 | 140 | 29.2 | 95.2 | 98.7 | 0.8 |
| 170 | 40 | 193 | 29.2 | 95.6 | 98.8 | 0.7 |
| 170 | 40 | 217 | 32.6 | 95.6 | 98.8 | 0.8 |

2) Example 10-2

1,4-BDO was prepared from GBL by hydrogenation. Specifically, H₂ and GBL were supplied to a reactor under the following conditions, and CuO(72.2)MnO₂(2.5)ZnO(0.3)SiO₂(25) (the values within the parentheses represent wt %), which was prepared as described in Example 1 of Korean Patent No. 10-0538979, was used as a catalyst.

Reaction Conditions: 170° C., 40 atm

Supply Conditions: H₂/GBL=32/1 m/m, WHSV=0.6 h⁻¹

A part of the product was recovered according to the reaction time and its components were analyzed. The results are shown in Table 31 below.

TABLE 31

| Reaction Time (h) | Conv. (%) | Selectivity (%) | | | | | 1,4-BDO Yield (%) |
|---|---|---|---|---|---|---|---|
| | | THF | 1-BuOH | Butyric acid | 1,4-BDO | Others | |
| 2 | 96.3 | 0.41 | 0.26 | 0.00 | 99.02 | 0.30 | 95.3 |
| 27 | 96.4 | 0.54 | 0.21 | 0.00 | 98.50 | 0.75 | 95.0 |
| 36 | 96.2 | 0.56 | 0.34 | 0.00 | 98.73 | 0.37 | 95.0 |
| 49 | 96.2 | 0.54 | 0.31 | 0.00 | 98.84 | 0.31 | 95.1 |
| 58 | 96.5 | 0.46 | 0.30 | 0.00 | 98.46 | 0.78 | 95.0 |
| 72 | 96.1 | 0.38 | 0.38 | 0.00 | 98.89 | 0.35 | 95.1 |

Example 11: Preparation of 1,4-BDO from Dialkyl Succinate 1,4-BDO was prepared from dimethyl succinate (DMS) by hydrogenation. Specifically, methanol/DMS (50/50 vol %) was used and CuO(72.2)MnO₂(2.5)ZnO(0.3)SiO₂(25) (the values within the parentheses represent wt %), which was prepared as described in Example 1 of Korean Patent No. 10-0538979, was used as a catalyst, and the reaction was performed under the conditions shown in Table 32 below. A part of the product was recovered and its components were analyzed. The results are shown in Table 32 below.

TABLE 32

| Reaction Conditions | | | | | | Selectivity (%) | | | |
|---|---|---|---|---|---|---|---|---|---|
| Reaction Pressure (atm) | Reaction Time (h) | WHSV ($h^{-1}$) | $H_2$/DMS (m/m) | Reaction Time (h) | Conv. (%) | THF | 1,4-BDO | GBL | Total |
| 40 | 180 | 0.3 | 60 | 47 | 95.8 | 5.9 | 72.7 | 10.9 | 89.5 |
| 40 | 180 | 0.3 | 80 | 56 | 99.4 | 4.5 | 81.0 | 9.7 | 95.2 |
| 40 | 180 | 0.3 | 90 | 72 | 99.6 | 3.8 | 82.2 | 9.5 | 95.5 |
| 35 | 180 | 0.3 | 90 | 93 | 97.6 | 4.9 | 76.0 | 15.2 | 96.1 |
| 40 | 185 | 0.3 | 100 | 151 | 99.6 | 5.37 | 80.3 | 13.0 | 98.7 |
| 40 | 180 | 0.3 | 100 | 101 | 99.3 | 4.3 | 82.9 | 10.8 | 98.0 |
| 40 | 170 | 0.3 | 100 | 161 | 73.8 | 2.71 | 60.4 | 13.7 | 76.8 |
| 40 | 175 | 0.3 | 100 | 177 | 94.8 | 4.95 | 78.4 | 10.6 | 94.0 |

Among the results of Table 32, the differences in reactivity according to the molar ratio of $H_2$/DMS are illustrated in graphs in FIG. 11, and the differences in reactivity according to reaction temperature are illustrated in graphs in FIG. 12.

Example 12: Preparation of 1,4-BDO from Gamma-Butyrolactone and Furanone 1,4-BDO was prepared from GBL and furanone by hydrogenation. Specifically, the reaction composition was the same as in Table 33 below, and the components were supplied to a reactor under the following conditions. The catalyst used was the same as in Example 11.

Feed: $H_2$/reactants=32.6 m/m, WHSV=0.6 $h^{-1}$

The reaction conditions were 180° C. and 40 atm, and a part of the product was recovered according to the reaction time and its components were analyzed. The results are shown in Table 33 below.

TABLE 33

| Reactants Composition (GBL:furanone, vol %) | Reaction Time (h) | Conv. (%) | Selectivity (%) | | Fraction of unreacted GBL:furanone | |
|---|---|---|---|---|---|---|
| | | | 1,4-BDO | THF | GBL | Furanone |
| Only GBL | 132 | 95.6 | 98.8 | 0.8 | — | — |
| 7:3 | 1 | 94.8 | 97.7 | 2.1 | — | — |
| | 3 | 86.8 | 97.9 | 1.46 | 99.8 | 0.2 |

Additionally, the above results are shown in graphs in FIG. 13.

Example 13: Preparation of Hydroxy-Gamma-Butyrolactone and Dialkyl Succinate from O-Succinylhomoserine 1) Example 13-1

Direct deamination and hydrolysis of O-succinylhomoserine (O-SH) were performed as shown in FIG. 14, and specifically, performed as follows.

First, water was used as a solvent. However, since the water solubility of O-SH is 8.7 g/L, an excess amount of O-SH injection at the initial stage of the reaction produces air bubbles of the inert gases ($N_2$, Ar, etc.) contained in the NO to be supplied as a reactant, or the nitrogen gas produced by deamination. Therefore, a small amount of O-SH was injected several times. The total amount of O-SH injected was 250 g and it was injected to a final concentration of O-SH to be 50 wt %.

Upon completion of the reaction, the product in the aqueous solution was analyzed and the results are shown in Table 34 below.

TABLE 34

| Conv. (%) | Decomposition | Maleic acid | 2(5H)-Furanone | 2,4-Dihydroxy-butanoic acid | Homoserine | Succinic acid | pH of Product |
|---|---|---|---|---|---|---|---|
| | | | Selectivity (%) | | | | |
| 99.9 | 2.6 | 0.4 | 0.9 | 49.4 | 0.3 | 46.9 | 0.6 |

As described in Table 34, it was confirmed that succinic acid was produced by the hydrolysis of O-SH, and simultaneously, 2,4-dihydroxy-butanoic acid was produced by the deamination of DL-HS. Additionally, since the precipitate produced by the final product was succinic acid, which has water solubility of 58 g/L (20° C.), it was confirmed that a part of the succinic acid produced by the reaction remained undissolved in the aqueous solution.

In the primary filtration process, succinic acid with a purity of 88.5% was recovered in about 64% yield, further washed with water, and succinic acid with a purity of 99.5% was thereby recovered. The residual solution, from which succinic acid was removed by the primary filtration process, contained 2,4-dihydroxy-butanoic acid, which contained 16.6% of succinic acid.

2) Example 13-2

The reaction was performed in the same manner as in Example 13-1, except that the product was not separated after direct deamination-hydrolysis of O-SH (30 g).

After removing water and acid from the product by distillation under reduced pressure, methanol (60 g) and conc. H$_2$SO$_4$ (2 g) were added thereto, and succinic acid was esterified while simultaneously cyclodehydrating 2,4-dihydroxy-butanoic acid by refluxing for 2 hours, and thereby hydroxy-gamma-butyrolactone and a mixture of dimethyl succinate and monomethyl succinate were prepared. The final products were subjected to GC analysis and the results are shown in Table 35 below.

TABLE 35

| | Products After Reaction | | | | | |
|---|---|---|---|---|---|---|
| | 2(5H)-Furanone | Dimethyl succinate | Monomethyl succinate | α-Hydroxy-γ-butyrolactone | Total | Others |
| Selectivity (mol %) | 1.5 | 45.2 | 4.1 | 42.7 | 93.8 | 6.2 |
| Boiling Point (° C. at 760 mmHg) | 203 | 196-200 | 259 | 249 | | |

Example 14: Preparation of Hydroxy-Gamma-Butyrolactone from Homoserine

DL-homoserine (250 g) and water (250 g) were added into a reactor and reacted at 25° C. under atmospheric pressure (1 atm) while injecting NO/O$_2$ gas thereto. Upon completion of the reaction, the results of components analysis of the reaction products were shown in Table 36 below.

TABLE 36

| Conv. (%) | Decomposition | Maleic acid | 2(5H)-Furanone | 2,4-Dihydroxy-butanoic acid | Homoserine | Succinic acid | pH of Product |
|---|---|---|---|---|---|---|---|
| | | | Selectivity (%) | | | | |
| 99.7 | 4.9 | 0.5 | 4.1 | 83.7 | 0.2 | 6.6 | 0.661 |

In the above products, HO-GBL (22.6%) and DMS (63%) were recovered from the final separated products obtained by cyclodehydration of 2,4-dihydroxy-butanoic acid and esterification of succinic acid, in the same manner as in Example 13-2, respectively.

Example 15: Preparation of Methoxy-Gamma-Butyrolactone from Homoserine

DL-homoserine (1 g), methanol (40 g), and Pt(5)/Ac (0.05 g) were added into a reactor and reacted under the conditions shown in Table 37. The results of components analysis of the products are shown in Table 37 below.

TABLE 37

| Reaction Pressure (atm) NO/N$_2$ (50/50 v/v) | H$_2$ | Reaction Temp (° C.) | Reaction Time (h) | Conv. (%) | Selectivity (%) | | | | | |
|---|---|---|---|---|---|---|---|---|---|---|
| | | | | | 4-Hydroxy-2-butenoic acid methylester | Furanone/ GBL | HO- GBL | MeO- GBL | 4-Hydroxy-2-methoxybutanoic acid | Others |
| 15 | 0 | 100 | 1.5 | 88.5 | 0.6 | 2.0 | 7.4 | 69.4 | 1.7 | 18.9 |
| 15 | 0 | 100 | 4 | 91.7 | 0.6 | 2.7 | 6.8 | 65.3 | 5.0 | 19.6 |
| 15 | 0 | 110 | 1.5 | 99.2 | 0.4 | 3.2 | 6.1 | 62.6 | 8.4 | 19.3 |

Additionally, the above results are shown in FIG. 15.

Example 16: Preparation of Hydroxy-Gamma-Butyrolactone from Homoserine

DL-homoserine (1 g), water (40 g), and Pt(5)/Ac (0.1 g) were added into a reactor, injected with NO/N$_2$ gas to have an internal pressure of 15 atm in the reactor, and reacted under the conditions shown in Table 38. The results of components analysis of the products are shown in Table 38 below.

TABLE 38

| Reaction Temp (° C.) | Reaction Time (h) | Conv. (%) | Selectivity (%) | | | |
|---|---|---|---|---|---|---|
| | | | Decomposition | Furanone | HO-GBL | Cl-GBL |
| 60 | 2 | 26.4 | 21.5 | 0 | 62.56 | 0 |
| 80 | 2 | 36.83 | 22.21 | 0 | 63.35 | 0 |
| 100 | 2 | 48.37 | 17.25 | 1.71 | 72.91 | 0 |
| 120 | 2 | 61.5 | 10.74 | 1.2 | 76.54 | 0 |
| 160 | 2 | 96.87 | 21.53 | 2.2 | 67.5 | 0 |

Additionally, the above results are illustrated in FIG. 16. As illustrated in Table 38 and FIG. 16, it was confirmed that HO-GBL could be prepared by simultaneously proceeding with deamination and cyclization.

The invention claimed is:

1. A process for preparing gamma-butyrolactone, a gamma-butyrolactone derivative, furanone, dialkyl succinate, a by-product, or a mixture thereof, comprising:
   reacting a solution of a homoserine-based compound with NO$_x$ (step 1); and
   recovering gamma-butyrolactone, a gamma-butyrolactone derivative, furanone, dialkyl succinate, a by-product, or a mixture thereof from the products obtained in step 1 (step 2),
   wherein, in step 1, x is any of 1, 1.5, 2, and 3.

2. The process according to claim 1, wherein NO$_x$, directly as a gas or in the form of an acid or salt, reacts with the homoserine-based compound in step 1.

3. The process according to claim 2, wherein the acid or salt is HNO$_3$, NH$_4$NO$_3$, NaNO$_2$, Fe(NO$_3$)$_3$, Al(NO$_3$)$_3$, Cu(NO$_3$)$_3$, Bi(NO$_3$)$_3$, Zn(NO$_3$)$_2$, or Pb(NO$_3$)$_2$.

4. The process according to claim 2, wherein the reaction with the NO$_x$ in step 1 is performed by injecting NO gas; or NO gas in combination with O$_2$ gas, an inert gas, or a mixture thereof.

5. The process according to claim 1, wherein the solvent for the solution of a homoserine-based compound is water, chloroform, dichloroform, methanol, halo-gamma-butyrolactone, or a mixture thereof.

6. The process according to claim 1, wherein the homoserine-based compound is homoserine, homoserine lactone, O-acetylhomoserine, O-succinyl homoserine, homoserine lactone hydrochloride, homoserine lactone hydrobromide, or a mixture thereof.

7. The process according to claim 1, wherein step 1 comprises adding a halide to the solution of a homoserine-based compound.

8. The process according to claim 1, wherein step 1 comprises further adding a metal catalyst to the solution of a homoserine-based compound.

9. The process according to claim 8, wherein the metal catalyst is at least one selected from M$_1$/X, M$_1$M$_2$/X, and Fe$_2$O$_3$, wherein each of M$_1$ and M$_2$ are not the same as each other and are a noble metal or a transition metal, and X is activated carbon or SiO$_2$.

10. The process according to claim 9, wherein the noble metal is Pd, Pt, Rh, Ir, Re, Ru, or Au, and the transition metal is Fe, Pb, Sb, Ag, Al, Cu, Ni, Cr, or Zn.

11. The process according to claim 1, wherein the gamma-butyrolactone derivative is halo-gamma-butyrolactone, hydroxy-gamma-butyrolactone, methoxy-gamma-butyrolactone, acetoxy-gamma-butyrolactone, or a mixture thereof.

12. The process according to claim 1, wherein the by-product is succinic acid, succinic anhydride, acetic acid, acetic anhydride, 2,4-dihydroxybutanoic acid, 4-hydroxy-2-butenoic acid methyl ester, 4-hydroxy-2-methoxybutanoic acid, 4-hydroxy-2-chlorobutanoic acid, or a mixture thereof, and is separated and recovered for recycling in the process.

13. The process according to claim 1, wherein step 2 comprises recovering halo-gamma-butyrolactone or hydroxy-gamma-butyrolactone by extracting with chloroform, dichloroform, methyl chloroform, or tetrachloroethane.

14. The process according to claim 13, wherein the residual solution obtained after recovering the halo-gamma-butyrolactone is recycled into step 1.

15. The process according to claim 1, wherein step 2 comprises recovering hydroxy-gamma-butyrolactone, furanone, or a mixture thereof from the residual solution obtained after recovering the gamma-butyrolactone, gamma-butyrolactone derivative, furanone, dialkyl succinate, and by-product.

16. The process according to claim 1, wherein step 2 comprises recovering a part of upper layer of the solution containing the products obtained in step 1.

17. The process according to claim 1, further comprising reacting halo-gamma-butyrolactone or hydroxy-gamma-butyrolactone among the gamma-butyrolactone derivatives with hydrogen in the presence of a hydrogenation catalyst, thereby converting into gamma-butyrolactone, furanone, a by-product, or a mixture thereof (step 3).

18. The process according to claim 17, wherein the by-product is at least one selected from the group consisting of 4-chlorobutyric acid, 3-chloropropanol, butyric acid, 4-bromobutyric acid, 3-bromopropanol, THF, 2-HO-THF, 1-PrOH, 2-PrOH, 1-BuOH, and 2-BuOH.

19. The process according to claim 17, wherein the hydrogenation catalyst is at least one selected from $M_1/X_1$, $M_1M_2/X_1$, $M_1/X_1X_2$, and $M_1M_2/X_1X_2$, wherein each of $M_1$ and $M_2$ are not the same as each other and are a noble metal or a transition metal, and each of $X_1$ and $X_2$ are not the same as each other and are activated carbon or a metal oxide.

20. The process according to claim 19, wherein the noble metal is Pd, Pt, Rh, Ir, Re, Ru, or Au, and the transition metal is Fe, Pb, Sb, Ag, Al, Cu, Ni, Cr, In, W, P, Te, or Zn.

21. The process according to claim 19, wherein the metal oxide is a mixed metal oxide comprising a material selected from the group consisting of Al, Zr, Si, and Ti, or a chemically modified metal oxide thereof, wherein the metal oxide is chemically modified with an inorganic acid ($PO_4$, $SO_4$).

22. The process according to claim 17, wherein step 3 is performed in the presence of at least one solvent selected from the group consisting of dioxane, gamma-butyrolactone, halo-gamma-butyrolactone, hydroxy-gamma-butyrolactone, diethylene glycol, dimethyl ether, dimethyl sulfoxide, and propylene carbonate.

23. The process according to claim 1, further comprising:
reacting hydroxy-gamma-butyrolactone among the gamma-butyrolactone derivatives with acetic acid, acetic anhydride, or acetyl chloride thereby converting into acetoxy-gamma-butyrolactone (step 4); and
heating the acetoxy-gamma-butyrolactone, thereby converting into gamma-butyrolactone, furanone, a by-product, or a mixture thereof (step 5).

24. The process according to claim 23, wherein the by-product is acrolein, butyl acetate, halo-gamma-butyrolactone, or a mixture thereof.

25. The process according to claim 1, further comprising:
reacting the gamma-butyrolactone or furanone with hydrogen in the presence of a metal catalyst, thereby converting into 1,4-butanediol (step 6).

26. The process according to claim 1, further comprising:
reacting the dialkyl succinate with hydrogen in the presence of a metal catalyst, thereby converting into 1,4-butanediol (step 7).

27. The process according to claim 25, wherein the metal catalyst is at least one selected from $M_1/X$ and $M_1M_2/X$, wherein each of $M_1$ and $M_2$ are not the same as each other and are a noble metal or a transition metal, and X is activated carbon or a metal oxide.

28. The process according to claim 27, wherein the noble metal is Pd, Pt, Rh, Ir, Re, Ru, or Au, and the transition metal is Fe, Pb, Sb, Ag, Al, Cu, Ni, Cr, or Zn.

29. The process according to claim 27, wherein the metal oxide is $Al_2O_3$, $ZrO_2$, $SiO_2$, or $TiO_2$.

* * * * *